United States Patent [19]

Caras et al.

[11] Patent Number: 5,759,775
[45] Date of Patent: Jun. 2, 1998

[54] METHODS FOR DETECTING NUCLEIC ACIDS ENCODING AL—1 NEUROTROPHIC FACTOR

[75] Inventors: Ingrid W. Caras, San Francisco; John W. Winslow, El Granada, both of Calif.

[73] Assignee: Genetech, Inc., South San Franscisco, Calif.

[21] Appl. No.: 442,248

[22] Filed: May 15, 1995

Related U.S. Application Data

[63] Continuation of Ser. No. 330,128, Oct. 27, 1994.
[51] Int. Cl.[6] .................. C12Q 1/68; C12P 19/34; C07H 21/04; C07H 21/02
[52] U.S. Cl. .................. 435/6; 435/91.2; 536/23.5; 536/24.31; 536/24.33
[58] Field of Search .................. 435/6, 91.2; 536/23.5, 536/24.31, 24.33

[56] References Cited

FOREIGN PATENT DOCUMENTS

| 597503 A2 | 5/1994 | European Pat. Off. ........ C07K 15/00 |
| WO 90/02798 | 3/1990 | WIPO . |
| WO 94/11384 | 5/1994 | WIPO .................. C07H 21/04 |
| WO 95/27060 | 10/1995 | WIPO .................. C12N 15/12 |

OTHER PUBLICATIONS

Cheng et al., "Identification and Cloning of ELF-1, a Developmentally Expressed Ligand for the Mek4 and Sek Receptor Tyrosine Kinases" *Cell* 79:157–168 ( Oct. 7, 1994).

Davis., "Ligands for EPH–Related Receptor Tyrosine Kinases That Require Membrane Attachment or Clustering for Activity" *Science* 266:816–819 (Nov. 4, 1994).

Winslow et al., "Cloning of AL–1, a Ligand for an Eph–Related Tyrosine Kinase Receptor Involved in Axon Bundle Formation" *Neuron* 14:973–981 (May 1995).

Bartley et al., "B61 is a ligand for the ECK receptor protein–tyrosine kinase" *Nature* 368:558–560 (Apr. 7, 1994).

Beckman et al., "Molecular characterization of a family ligands for eph–related tyrosine kinase receptors" *EMBO Journal* 13(16):3757–3762 (1994).

Berkemeier et al., "Neurotrophin-5: A Novel Neurotrophic Factor That Activates trk and trkB" *Neuron* 7:857–866 ( Nov. 1991).

Byrn et al., "Biological properties of a CD4 immunoadhesin" *Nature* 344:667–670 (Apr. 12, 1990).

Capon et al., "Designing CD4 immunoadhesins for AIDS therapy" *Nature* 337:525–531 (Feb. 9, 1989).

Gilardi–Hebenstreit et al., "An Eph–related receptor protein tyrosine kinase gene segmentally expressed in the developing mouse hindbrain" *Oncogene* 7:2499–2506 (1992).

Hefti, Franz, "Nerve Growth Factor Promotes Survival of Septal Cholinergic Neurons After Fimbrial Transactions" *J. of Neuroscience* 6(8):2155–2162 (Aug. 1986).

Heumann, Rolf, "Regulation of the Synthesis of Nerve Growth Factor" *J. Exp. Biol.* 132:133–150 (1987).

Kaisho et al., "Cloning and expression of a cDNA encoding a novel human neurotrophic factor"*FEBS Letters* 266(1, 2):187–191 (Jun. 1990).

Lai et al., "An extended Family of Protein–Tyrosine Kinase genes Differentially Expressed in the Vertebrate Nervous System" *Neuron* 6:691–704 (May 1991).

(List continued on next page.)

*Primary Examiner*—Stephanie W. Zitomer
*Assistant Examiner*—Paul B. Tran
*Attorney, Agent, or Firm*—Timothy E. Torchia

[57] ABSTRACT

Provided are nucleic acids encoding AL-1 protein, as well as AL-1 protein produced by recombinant DNA methods. Such AL-1 protein is useful in preparing antibodies and in diagnosing and treating various neuronal disorders. The present invention provides methods to preferentially detect or amplify AL-1 nucleic acid in a sample using AL-1 nucleotide sequence probes.

18 Claims, 7 Drawing Sheets

OTHER PUBLICATIONS

Leibrock et al., "Molecular cloning and expression of brain-derived neurotrophic factor" *Nature* 341:149–152 (Sep. 14, 1989).

Maisonpierre et al., "Ehk-1 and Ehk-2: two novel members of the Eph receptor–like tyrosine kinase family with distinctive sructures and neuronal epression" *Oncogene* 8:3277–3288 (1993).

Maisonpierre et al., "Neurotrophin-3: A Neurotrophic Factor Related to NGF and NGF and BDNF" *Science* 247:1446–1451 (Mar. 23, 1990).

Rosenthal et al., "Primary Structure and Biological Activity of a Novel Human Neurotrophic Factor" *Neuron* 4:767–773 (May 1990).

Thoenen et al., "Physiology of Nerve Growth Factor" *Physiological Reviews* 60(4):1384–1335 (Oct 1980).

Tuzi et al., "eph, the largest known family of punative growth factor receptors" *Br. J. Cancer* 9:417–421 (1994).

Zhou et al., "Isolation and Characterization of Bsk, a Growth Facator Receptor–like Tyrosine Kinase Associated With the Limbic System" *J. of Neur. Res.* 37:129–143 (1994).

Leslie et al. Proc. Natl. Acad. Sci. (U.S.A.) 87(15):5822–5826, 1990.

Cheng et al. Cell 79:157–168, 1994 (Oct. 7).

Saiki et al. Science 239:487–491, 1988.

```
  1  AGCCCCCAGT CCTCTAGACA CTCTGCTTGC TTTTTCCCCG CTTCCCGCCG CCTTTTTTTT TTTACGAAAA ACATCATCTA GATTAAGAT GACTCGTCTT
101  CTTTAATCTC GTCCGTATCA GCACTGAAGA CTGAAAGGGA ACCTTCACCA CCACTCCAAC CCTGGTGGGG GCTTAAAAAA AAAAAATAAC AGTTCTAAAA
201  AAGAAAGGGG GACCAAAAAA CAGAAAAAGG AAAGTCTTAA GAGGCAAAGG AGCGGGACTC GGGACCCTCT GCAGACCCTT GACTCAGCCC ACCCAGGACC
301  GTACTAGCCA TCCGAACTTC TAATTCATCT AAAGGGAGGG CGGCACAAGC CAGAAGCAAA CTTCGGCGGT CTCTGCGGAT CTGTGATTCC
401  CACATTGAGA GGGGTCGAGA GCCTAAGAGC ACAGGACCCC ACCAGGAGGA GCAGAAGAGG GCCTCTCTCG CCCCTTCCAC CAAGCCTGAA CCTTAGACTG
501  AACCACGCGG GACCTAAGAG GCAGAAGAGG GTAGTAGAAA ATG CGG GGC TCC GGG CCC CGC GGT GCG GGA CGC CGA CGG ACC CAG GGC
  1                                              Met Arg Gly Ser Gly Pro Arg Gly Ala Gly Arg Arg Thr Gln Gly

589  AGA GGT GGC GGC GAC ACC CCC CGC GTC CCT CTG GCA GGC TGC TAT TCC GCA CCT CTA AAG GGG CCC CTC TGG
 17  Arg Gly Gly Gly Asp Thr Pro Arg Val Pro Leu Ala Gly Cys Tyr Ser Ala Pro Leu Lys Gly Pro Leu Trp

670  ACG TGC CTT CTC CTG TGT GCG GCG CTT TTG GCC AGC CCC AGT AAC GAA GTG AAT TTA GAT GAA CTG TCG CGC ACT
 44  Thr Cys Leu Leu Leu Cys Ala Ala Leu Arg Thr Leu Leu Ala Ser Pro Ser Asn Glu Val Asn Leu Asp Ser Arg Thr

751  GTC CTG GGA GAC CTT GGA ATT GCT TTT CCA AAG GTT ATG GAA CAG AAT CAG AAT GGG GAA GTT GAT GAA AAC TAT CCC CCC
 71  Val Leu Gly Asp Leu Gly Ile Ala Phe Pro Lys Val Met Glu Gln Asn Gln Asn Gly Glu Val Asp Glu Asn Tyr Pro Pro

832  ATC CAC ACC TAT CAA GTG TGC AAA GTT CTG AAA TTT GAA CTC GAA CTC GAA ATT TGG CTG TTG ACC AGT TGG ATC TCT AAC GAA GGT
 98  Ile His Thr Tyr Gln Val Cys Lys Val Leu Lys Phe Glu Leu Glu Leu Glu Ile Trp Leu Leu Thr Ser Trp Ile Ser Asn Glu Gly

913  GCT TCC AGA ATT TTT ATT GAA CTC AAG TTT ACT CTG AGG GAT TGC AAC AGC CTT CCT GGA GGA CTG GGG ACT TGC AAG GAG
125  Ala Ser Arg Ile Phe Ile Glu Leu Lys Phe Thr Leu Arg Asp Cys Asn Ser Leu Pro Gly Gly Leu Gly Thr Cys Lys Glu

994  ACC TTT AAC ATG TAT TAT TTT GAG TCG GAT GAT GAG AAT GGG AGA AAT ATC AAA GAG AAC CAG ATC TAC AAG ATC GAT ACC
152  Thr Phe Asn Met Tyr Tyr Phe Glu Ser Asp Asp Glu Asn Gly Arg Asn Ile Lys Glu Asn Gln Ile Tyr Lys Ile Asp Thr
```

*FIG._1A*

```
1075  ATT GCT GCT GAT GAG AGC TTC ACC GAA CTT GGA GAC CGG GTC ATG AAG CTG AAT ACG GAG GTC AGA GAT GTA GGA
 179  Ile Ala Ala Asp Glu Ser Phe Thr Glu Leu Gly Asp Arg Val Met Lys Leu Asn Thr Glu Val Arg Asp Val Gly

1156  CCT CTG AGC AAA AAG GGA TTT TAT CTT GCT TTC CAA GAT GTC GGT GCT CTG GTT TCT GTC CGT GTC TAC TAT
 206  Pro Leu Ser Lys Lys Gly Phe Tyr Leu Ala Phe Gln Asp Val Gly Ala Leu Val Ser Val Arg Val Tyr Tyr

1237  AAA AAA TGT CCT TCT GTA GTT AGA CAT TTG CTT CCT GAC ACG ATC ACT GGA GCA GAT TCT TCC CAG TTG CTA GAG
 233  Lys Lys Cys Pro Ser Val Val Arg His Leu Ala Val Phe Pro Asp Thr Ile Thr Gly Ala Asp Ser Ser Gln Leu Leu Glu

1318  GTG TCA GGC TCC TGC GTC AAC CAT TCT GTG ACA GAC CCT CCC AAA ATG CAT TGC AGT GCT GAA GGG GAG TGG CTG GTT
 260  Val Ser Gly Ser Cys Val Asn His Ser Val Thr Asp Pro Pro Lys Met His Cys Ser Ala Glu Gly Glu Trp Leu Val

1399  CCC ATC GGG AAA TGC ATG TGC AAG GCC GAA TAT GAG AAA AAT GGT ACC TGT CAA GTG TGC AGA CCT TCC ACC TGT GTC TGT
 287  Pro Ile Gly Lys Cys Met Cys Lys Ala Glu Tyr Glu Lys Asn Gly Thr Cys Gln Val Cys Arg Pro Ser Thr Cys Val Cys

1480  GCC TCT CCT CAC AGC CAG ACC TGC AGC AAA TGT CCA CCT CAC GAG GAA GCT CCT TCT CCA GTC ACC AAC GTG AAG AAG
 314  Ala Ser Pro His Ser Gln Thr Cys Ser Lys Cys Pro Pro His Glu Glu Ala Pro Ser Pro Val Thr Asn Val Lys Lys

1561  GAA AAG GAT TAT TTC AGG AGG GAA TCT GAT CCG CCC CCC ACA ATG GCA TGC ACA GTC ACC CCA ACT CTG GAG TAC GAA ATC
 341  Glu Lys Asp Tyr Phe Arg Arg Glu Ser Asp Pro Pro Pro Thr Met Ala Cys Thr Val Thr Pro Thr Leu Glu Tyr Glu Ile

1642  GGG AAG ATC GCA AAG AAC AGC ATT TCT TTT CTT AGC CCA CAA GAG CCA GAT CGC CCC AAT GGG ATC ATT ACG GCA GAG AAA
 368  Gly Lys Ile Ala Lys Asn Ser Ile Ser Phe Leu Ser Pro Gln Glu Pro Asp Arg Pro Asn Gly Ile Ile Leu Glu Tyr Glu Ile

1723  AAG TAC TTT GAA AAG GAC CAA ATT ATC AAG GAG ACC ACT ACA GAG ACC TCT AAA GAG ACA ATT ACG GCA GAG CTG AAA
 395  Lys Tyr Phe Glu Lys Asp Gln Ile Ile Lys Glu Thr Thr Thr Ile Thr Ala Glu Gly Leu Lys

1804  CCT GCG TCT GTG TAT GTC TTC CAA ATT CGA ACA GCA GCA CGT ACA GCA GGC TAC GGC GTC TTC AGT CGA CGG TTT GAG TTT GAA
 422  Pro Ala Ser Val Tyr Val Phe Gln Ile Arg Thr Ala Ala Arg Thr Ala Gly Tyr Gly Val Phe Ser Arg Arg Phe Glu Phe Glu
```

```
1885  ACC ACA CCA GTG TCA GTT GCA GCA TCT AAT GAT CAA AGC CAG ATT CCC ATC ATT GCG GTG TCA GTG GGA GTC ATC
 449  Thr Thr Pro Val Ser Val Ala Ala Ser Asn Asp Gln Ser Gln Ile Pro Ile Ile Ala Val Ser Val Gly Val Ile

1966  TTG GCA ATG ATC GGC TTC CTC CTC TTT GGG AGG GCT TGT TGC TGT GAA AAG ATG CAC TTT GCT
 476  Leu Ala Met Ile Gly Phe Leu Leu Phe Gly Arg Ala Ser Ser Lys Met His Phe Ala

2047  GTT GCC CAT CCA AGC CTA ATA TGG CGG TGT GGC TAC CGT TAC AGC AAA GCA GAA CAG GAT CCA GAA AAG ATG CAC TTT CAT
 503  Val Ala His Pro Ser Leu Ile Trp Arg Cys Gly Tyr Ser Lys Ala Glu Gln Asp Pro Glu Lys Met His Phe His

2128  AAC GGG CAC ATT AAA CTG CCA GGA GTA AGA ACG TAC ATT GAT CCA CAC ACC TAC GAA GAT CCC ACT CAA GCC GTT CAT GAA
 530  Asn Gly His Ile Lys Leu Pro Gly Val Arg Thr Tyr Ile Asp Pro His Thr Tyr Glu Asp Pro Thr Gln Ala Val His Glu

2209  TTT GCC AAG GAG ATC GAG GCC TCA TGC ATC ACC ATT GAG AGA GTT ATT GGA GCA GGT GAA TTT GGT GAA GTT TGT AGT GGA
 557  Phe Ala Lys Glu Ile Glu Ala Ser Cys Ile Thr Ile Glu Arg Val Ile Gly Ala Gly Glu Phe Gly Glu Val Cys Ser Gly

2290  CGT TTG AAA CTA CCC GGA AAA AGA GAA GCG AGT GGC TAC ACT GGC TAC GAA CTA CAT CTT GAA GGC GTT GTG ACT AAA AGT
 584  Arg Leu Lys Leu Pro Gly Lys Arg Glu Ala Ser Gly Tyr Thr Gly Tyr Glu Leu His Leu Glu Gly Val Val Thr Lys Ser

2371  GAT TTT CTG AGT GAA GCG AGT ATC ATG GGG CAG TTT GAT CAT CCA AAC ATC TTT TTA AAG AAA AAC GAT GGC CAG TTC ACT
 611  Asp Phe Leu Ser Glu Ala Ser Ile Met Gly Gln Phe Asp His Pro Asn Ile Phe Leu Lys Lys Asn Asp Gly Gln Phe Thr

2452  AAA CCT GTG ATG ATA GTG GAG TAC ATG ACA GAG AAT GGC TCC TTA GAC AGT TTC CTT GTG AAG TAC CTT TCT GAC ATG AAG
 638  Lys Pro Val Met Ile Val Glu Tyr Met Thr Glu Asn Gly Ser Leu Asp Ser Phe Leu Lys Tyr Leu Ser Asp Met Lys

2533  GTG ATT CAG CTT GTT GGC ATG TGT CTG GCA GGA ATC GCT GCA GGA ATG AAG TAC CTT GCG TCT GAC ATG ACG ACG GAC
 665  Val Ile Gln Leu Val Gly Met Cys Leu Arg Met Lys Tyr Leu Ala Ala Gly Met Lys Tyr Leu Ser Asp Met Lys Arg Asp

2614  CTT GCT GCT AGA AAC ATC TTA ATC AAC AGT AAC CTT GTG TGC AAA GTG TCT GAC TTC GGA CTT TCC AGG GTG CTG GAA GAT
 692  Leu Ala Ala Arg Asn Ile Leu Ile Asn Ser Asn Leu Val Cys Lys Val Ser Asp Phe Gly Leu Ser Arg Val Leu Glu Asp
```

```
2695 GAT CCT GAG GCA GCC TAT ACC ACA AGG GGA GGC AAA ATT CCA ATC AGG TGG ACT GCT CCA GAA GCA ATA GCT TTT CGA AAG
 719 Asp Pro Glu Ala Ala Tyr Thr Thr Arg Gly Gly Lys Ile Pro Ile Arg Trp Thr Ala Pro Glu Ala Ile Ala Phe Arg Lys

2776 TTT ACC TCT GCC AGT GAT GTC TGG AGC TAT GGA ATC GTA ATG TGG GAA GTT GTG TCC TAT GGA GAG AGA CCG TAC TGG GAG
 746 Phe Thr Ser Ala Ser Asp Val Trp Ser Tyr Gly Ile Val Met Trp Glu Val Val Ser Tyr Gly Glu Arg Pro Tyr Trp Glu

2857 ATG ACC AAT CAG GAT GTG ATC AAG GCA GTG GAA GAA GGC TAC CGC CTG CCA AGC CCC ATG GAT TGT CCT GCT GCC CTC TAT
 773 Met Thr Asn Gln Asp Val Ile Lys Ala Val Glu Glu Gly Tyr Arg Leu Pro Ser Pro Met Asp Cys Pro Ala Ala Leu Tyr

2938 CAA TTA ATG CTG GAT TGC TGG CAG AAA GAT CGC AAC AGC AGG CCC AAG TTT GAT CAC ATA GTC AAC ATG CTG GAT AAG CTG
 800 Gln Leu Met Leu Asp Cys Trp Gln Lys Asp Arg Asn Ser Arg Pro Lys Phe Asp His Ile Val Asn Met Leu Asp Lys Leu

3019 ATA CGA AAC CCA AGT AGT TTG AAG ACA GTA TCA GTG AAC TGG CTA GTA GGT GAA TCA GGT GTG GCT CAG ATT TTC ATG GAA AAT
 827 Ile Arg Asn Pro Ser Ser Leu Lys Thr Val Asn Ala Ser Arg Val Ser Thr Leu Ala Glu His Gly Ser Leu

3100 GGG TCT GGG GCC TAC AGA TCA GTA GGT GAA TGG CTA GTA GGT GAA TCA GGT GTG GCT CAG GTG GCT CGG TAC ACA GAG ATT TTC ATG GAA AAT
 854 Gly Ser Gly Ala Tyr Arg Ser Val Gly Glu Trp Leu Glu Val Gly Val Ala Gln Val Ala Arg Tyr Thr Glu Ile Phe Met Glu Asn

3181 GGA TAC AGT TCA ATG GAC GCT GTG GCT CAG GTG GCT GAC GTG ACC TTG GAG GAT TTG AGA CGC CTG GGA CTG GTC GGT CAC CAG
 881 Gly Tyr Ser Ser Met Asp Ala Val Ala Gln Val Ala Asp Val Thr Leu Glu Asp Leu Arg Arg Leu Gly Leu Val Gly His Gln

3262 AAG AAG ATC ATG ATG AAC AGC CTT CAA GAG ATG CAG CTG GTA AAC GTG AAG GTG ATG GTG TGA CCC GCA CAC GGG T
 908 Lys Lys Ile Met Asn Ser Leu Gln Glu Met Gln Leu Val Asn Val Lys Val Met Gly Met Val Pro Val OP*

3341 CACTTCTCCA AGTGAACAAC TCTGCACTTT GTAAACAGCC CTAAGATTTA TTTAACAGA GAAAGGGAAA TGGGTGGTTC CTAAACCTTT GAAGGCACTT

3441 GTCTCATCCT TTGACTTATA ATCAACATTT TACTAAAATC TCCAGATCTT CTTCTTAATG TCTTCGTTTT TTTCACTATG TAAATGTAAC CTGCGAAGAG

3541 AGCTAACATG AGAAACAACA ACATAGTAAC TCCTATAAAA ACATAGTAAC TAAATCTTTC TCCACTTGCA GCCCCTTTCA AAACTACCAG GGATCGACTT GAAAGGAAAA
```

FIG._1D

3641 GTTTAAAGC CATGTGTGGG CAAAGAAACG CTGCATTTA CTGACGTTTA TATTGTCTG CATAAGTGTA TTGGAGAGCA ATATGATTAG

3741 ATTATTTCTT AAATACAGTT TGTAATTTAA AATGGAATTA CATGTTATAA GTTATAGAAA ATAGTTTACA GACATGTTGC CCGGTCAAGG AAAAGTTCAG

3841 CACAGGGTGT ATATTTATTT TTCTGTGTTA TATAATTTAC TTTTAGTTGC ACTTCTAGAG AGTATTAGGC AATGAATGTG TATAGACTGT ATAGTTTGCA

3941 ATATACCGAG GAATGGACTT AAATTGGAAA TGTATGTATA TGTGCGTATG TGTGTGTGTG TTTGAATATG TAGATGGTAT TGTTCTGCTT

4041 GCCTTTTGTA TAGGGTTTTA ATTTGGCCCT CATACAGCAA AGGGTGTTCT AGACTATTTT ATGGGTAAGA GGAATAGGAA GCCCTTAGACC AAATTTCCCT

4141 CAAGTAGGTG TCCTTTCTCT CATT

*FIG._1E*

```
  1 ATTCCCCCGCCCTGCGCCGCCACCACACACGCCTTCTCTCCATCTTGTGAT
 61 TCCTTTTCCTCCTGAACCCTCCAGTGGGGTGCGAGTTTGTCTTTATCACCCCCATCC
121 CACCGCCTTCTCTTTTCGCCTCTCCTTACCCCTCCCCAGCTTGGTGGGCGCCTCTTCC
181 TTTCTCGCCCCCCTTTCATTTTTATTATTCATATTTATTTGGCGCCCGCTCTCTCTGT
241 CCCTTTGCCCTGCCCTCCCCCGGATCCCCGCTCTCTCCCCGAGTGGCGCGTCGGGG
301 GCTCCGCCGCTGGCCAGGCGTGATGTTGCACGTGGAGATGTTGACGTGGTGTTTCTGT
  1                      M  L  H  V  E  M  L  T  L  V  F  L  V
361 GCTCTGGATGTGTGTGTTCAGCCCAGGACCCCGGCTCCAAGGCCGTCGCCGACCGCTACGC
 14  L  W  M  C  V  F  S  Q  D  P  P  G  S  K  A  V  A  D  R  Y  A
421 TGTCTACTGGAACAGCAGCAACCCCAGATTCCAGAGGGGTGACTACCATATTGATGTCTG
 34  V  Y  W  N  S  S  N  P  R  F  Q  R  G  D  Y  H  I  D  V  C
481 TATCAATGACTACCTGGATGTTTTCTGCCCTCACTATGAGGACTCCGTCCCAGAAGATAA
 54  I  N  D  Y  L  D  V  F  C  P  H  Y  E  D  S  V  P  E  D  K
541 GACTGAGCGCTATGTGCTCTACATGGTGAACTTTGATGGCTACAGTGCCTGCGACCACAC
 74  T  E  R  Y  V  L  Y  M  V  N  F  D  G  Y  S  A  C  D  H  T
601 TTCCAAAGGGTTCAAGAGATGGGAATGTAACCGGCCTCACTCTCCAAATGGACCGCTGAA
 94  S  K  G  F  K  R  W  E  C  N  R  P  H  S  P  N  G  P  L  K
661 GTTCTCTGAAAAATTCCAGCTCTTCACTCCCTTTTCTCTAGGATTTGAATTCAGGCCAGG
114  F  S  E  K  F  Q  L  F  T  P  F  S  L  G  F  E  F  R  P  G
721 CCGAGAATATTTCTACATCTCCCTGCAATCCCAGATAATGGAAGAAGGTCCTGTCTAAA
134  R  E  Y  F  Y  I  S  A  I  P  D  N  G  R  R  S  C  L  K
```

FIG._2A

```
781  GCTCAAAGTCTCTTTGTGAGACCAACAAATAGCTGTATGAAAACTATAGGTGTTCATGATCG
154   L  K  V  F  V  R  P  T  N  S  C  M  K  T  I  G  V  H  D  R

841  TGTTTTCGATGTTAACGACAAAGTAGAAAATTCATTAGAACCAGCAGATGACACCGTACA
174   V  F  D  V  N  D  K  V  E  N  S  L  E  P  A  D  D  T  V  H

901  TGAGTCAGCCGAGCCATCCCGCGGCGAGAACGCGGCACAAACACCAAGGATACCCAGCCG
194   E  S  A  E  P  S  R  G  E  N  A  A  Q  T  P  R  I  P  S  R

961  CCTTTTGGCAATCCTACTGTTCCTCCTGGCGATGCTTTTGACATTATAGCACAGTCTCCT
214   L  L  A  I  L  F  L  L  A  M  L  L  T  L  0

1021 CCCATCACTTGTCACAGAAAACATCAGGGTCTCTTGGAACACCAGAGATCCACCTAACTGCT
1081 CATCCTAAGAAGGGACTTGTTATTGAACTTGTCAGATGTCAGATTTTTGGTTTTCTTTCT
1141 TTCAGCCTGAATTCTAAGCAACAACCTTCAGGTTGGGGGCCCTTGGCTTCTCTCACCCTGCCCTCCC
1201 TCACCCACCCCGCCCCACCCCAGCCCTTGGCTTCATAGTGACACCAGTGGTTCGTCAGCTCC
1261 AAATGGACTCTCCTCCAGATGAAAATGCCAAATTGTCCGTTAGCGCACTGTGTCAGCGGGCTAGTGGACA
1321 TGTGCATTCTCCTCTAAGAACTCCACCTCCGTTAGCGCACTGTGTCAGCGGGCTATGGACA
1381 AGGAAGAATAGTGGCAGATGCCTTTCATTCAGAACTGTAAGATGATCGCGCAGGGCATCATGTCA
1441 ATGCAATATATTTATGCCTTCAGGAGGGAGGTTCAGATGATACGATATTACACCATTCCTATA
1501 CCATGTCAGGTCCGGAATGAACAGGCTTCTGACASCCCCAACTTGCTCTCTAAAAGAAGCCTTTTTTTT
1561 GGAGTATGTAAATGAACATTCTTGACASCCCCAACTTGTGCTCTCTAAAAGAAGCCTTTTTTTT
1621 ACTGTCTTAAAGCATTCTTGACACAGTGGGGGGTGTGTATGTGAGTGTAATACAGAGCAGGTGWAAACAGAGAAA
1681 TTTCTAGGAGACAGAGTGGGGGGTGTGTATGTGAGTGCCTCTAATTTTTTTTGGTGACTGGGC
1741 ACTACAGGTTTGCTGGGGGTGTGTATGTGAGTGCCTCTAATTTTTTTTGGTGACTGGGC
1801 AGTGCACACCAGATATTTTTCTTTGAATACAGATCACG
```

FIG._2B

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 4165 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AGCCCCCAGT  CCTCTAGACA  CTCTGCTTGC  TTTTCCCCG   CTTCCCGCCG         50

CCTTTTTTTT  TTTACGGAAA  ACATCATCTA  GATTTAAGAT  GACTCGTCTT        100

CTTTAATCTC  GTCCGTATCA  GCACTGAAGA  CTGAAAGGGA  ACCTTCACCA        150

CCACTCCAAC  CCTGGTGGGG  GCTTAAAAAA  AAAAAATAAC  AGTTCTAAAA        200

AAGAAAGGGG  GACCAAAAAA  CAGAAAAAGG  AAAGTCTTAA  GAGGCAAAGG        250

AGCGGGACTC  GGGACCCTCT  GCAGACCCTT  GACTCAGCCC  ACCCAGGACC        300
```

| | | | | | |
|---|---|---|---|---|---|
| GTACTAGCCA | TCCGAACTTC | TAATTCATCT | TATCCAACTG | AAAGGGAGGG | 350 |
| CGGCACAAGC | CAGAAGCAAA | CTTCGGCGGT | CTCTGCGGAT | CTGTGATTCC | 400 |
| CACATTGAGA | GGGGTCGAGA | GCCAGAAGGC | ACAGGACCCC | ACCAGGAGGA | 450 |
| GGAGTTCCGC | GCCTCTCTCG | CCCCTTCCAC | CAAGCCTGAA | CCTTAGACTG | 500 |
| AACCACGCGG | GACCTAAGAG | GCAGAAGAGG | GTAGTAGAAA | ATGCGGGGCT | 550 |
| CCGGGCCCCG | CGGTGCGGGA | CGCCGACGGA | CCCAGGGCAG | AGGTGGCGGC | 600 |
| GGCGACACCC | CCCGCGTCCC | TGCCTCTCTG | GCAGGCTGCT | ATTCCGCACC | 650 |
| TCTAAAGGGG | CCCCTCTGGA | CGTGCCTTCT | CCTGTGTGCG | GCGCTCCGGA | 700 |
| CCCTTTTGGC | CAGCCCCAGT | AACGAAGTGA | ATTTATTGGA | TTCGCGCACT | 750 |
| GTCCTGGGAG | ACCTTGGATG | GATTGCTTTT | CCAAAGAATG | GGTGGGAAGA | 800 |
| GATTGGTGAA | GTTGATGAAA | ACTATCCCCC | CATCCACACC | TATCAAGTGT | 850 |
| GCAAAGTTAT | GGAACAGAAT | CAGAATAATT | GGCTGTTGAC | CAGTTGGATC | 900 |
| TCTAACGAAG | GTGCTTCCAG | AATTTTTATT | GAACTCAAGT | TTACTCTGAG | 950 |
| GGATTGCAAC | AGCCTTCCTG | GAGGACTGGG | GACTTGCAAG | GAGACCTTTA | 1000 |
| ACATGTATTA | TTTGAGTCG | GATGATGAGA | ATGGAGAAA | TATCAAAGAG | 1050 |
| AACCAGTACA | TCAAGATCGA | TACCATTGCT | GCTGATGAGA | GCTTCACCGA | 1100 |
| ACTTGACCTT | GGAGACCGGG | TCATGAAGCT | GAATACGGAG | GTCAGAGATG | 1150 |
| TAGGACCTCT | GAGCAAAAAG | GGATTTTATC | TTGCTTTCCA | AGATGTCGGT | 1200 |
| GCTTGCATCG | CTCTGGTTTC | TGTCCGTGTC | TACTATAAAA | AATGTCCTTC | 1250 |
| TGTAGTTAGA | CATTGGCTG | TTTTCCCTGA | CACGATCACT | GGAGCAGATT | 1300 |
| CTTCCCAGTT | GCTAGAGGTG | TCAGGCTCCT | GCGTCAACCA | TTCTGTGACA | 1350 |
| GACGATCCTC | CCAAAATGCA | TTGCAGTGCT | GAAGGGAGT | GGCTGGTTCC | 1400 |
| CATCGGGAAA | TGCATGTGCA | AGGCCGGATA | TGAAGAGAAA | AATGGTACCT | 1450 |
| GTCAAGTGTG | CAGACCTGGG | TTCTTCAAAG | CCTCTCCTCA | CAGCCAGACC | 1500 |
| TGCAGCAAAT | GTCCACCTCA | CAGTTACACC | CATGAGGAAG | CTTCCACCTC | 1550 |
| TTGTGTCTGT | GAAAAGGATT | ATTTCAGGAG | GGAATCTGAT | CCGCCCACAA | 1600 |
| TGGCATGCAC | AACTCCTTCT | CCAGTCACCA | ACGTGAAGAA | GGGGAAGATC | 1650 |
| GCAAAGAACA | GCATTTCTTT | GTCTTGGCAA | GAGCCAGATC | GCCCCAATGG | 1700 |
| GATCATCCTG | GAGTACGAAA | TCAAGTACTT | TGAAAAGGAC | CAAGAGACCA | 1750 |
| GCTACACAAT | TATCAAGTCT | AAAGAGACCA | CTATTACGGC | AGAGGGCCTG | 1800 |
| AAACCTGCGT | CTGTGTATGT | CTTCCAAATT | CGAGCACGTA | CAGCAGCAGG | 1850 |
| CTACGGCGTC | TTCAGTCGAC | GGTTTGAGTT | TGAAACCACA | CCAGTGTCAG | 1900 |
| TTGCAGCATC | TAATGATCAA | AGCCAGATTC | CCATCATTGC | GGTGTCAGTG | 1950 |
| ACGGTGGGAG | TCATCTTGTT | GGCAGTGATG | ATCGGCTTCC | TCCTCAGTGG | 2000 |
| CAGTTGCTGC | GAATGTGGCT | GTGGGAGGGC | TTCTTCCCTG | TGCGCTGTTG | 2050 |
| CCCATCCAAG | CCTAATATGG | CGGTGTGGCT | ACAGCAAAGC | AAAGCAGGAT | 2100 |
| CCAGAAGAGG | AAAAGATGCA | CTTTCATAAC | GGGCACATTA | AACTGCCAGG | 2150 |
| AGTAAGAACG | TACATTGATC | CACACACCTA | CGAAGATCCC | ACTCAAGCCG | 2200 |
| TTCATGAATT | TGCCAAGGAG | ATCGAGGCCT | CATGCATCAC | CATTGAGAGA | 2250 |
| GTTATTGGAG | CAGGTGAATT | TGGTGAAGTT | TGTAGTGGAC | GTTTGAAACT | 2300 |

| | | | | | |
|---|---|---|---|---|---|
| ACCCGGAAAA | AGAGAATTGC | CTGTGGCTAT | CAAAACTCTT | AAAGTAGGCT | 2350 |
| ACACTGAAAA | GCAGCGCAGA | GATTTTCTGA | GTGAAGCGAG | TATCATGGGG | 2400 |
| CAGTTTGATC | ATCCAAACAT | CATCCATCTA | GAAGGCGTTG | TGACTAAAAG | 2450 |
| TAAACCTGTG | ATGATAGTGA | CAGAGTACAT | GGAGAATGGC | TCCTTAGACA | 2500 |
| CATTTTTAAA | GAAAAACGAT | GGCCAGTTCA | CTGTGATTCA | GCTTGTTGGC | 2550 |
| ATGCTGAGAG | GCATCGCTGC | AGGAATGAAG | TACCTTTCTG | ACATGGGCTA | 2600 |
| CGTGCACAGA | GACCTTGCTG | CTAGAAACAT | CTTAATCAAC | AGTAACCTTG | 2650 |
| TGTGCAAAGT | GTCTGACTTT | GGACTTTCCA | GGGTGCTGGA | AGATGATCCT | 2700 |
| GAGGCAGCCT | ATACCACAAG | GGGAGGCAAA | ATTCCAATCA | GATGGACTGC | 2750 |
| TCCAGAAGCA | ATAGCTTTC | GAAAGTTTAC | CTCTGCCAGT | GATGTCTGGA | 2800 |
| GCTATGGAAT | CGTAATGTGG | GAAGTTGTGT | CCTATGGAGA | GAGACCGTAC | 2850 |
| TGGGAGATGA | CCAATCAGGA | TGTGATCAAG | GCAGTGGAAG | AAGGCTACCG | 2900 |
| CCTGCCAAGC | CCCATGGATT | GTCCTGCTGC | CCTCTATCAA | TTAATGCTGG | 2950 |
| ATTGCTGGCA | GAAAGATCGC | AACAGCAGGC | CCAAGTTTGA | TGACATAGTC | 3000 |
| AACATGCTGG | ATAAGCTGAT | ACGAAACCCA | AGTAGTTTGA | AGACACTGGT | 3050 |
| GAACGCGTCA | AGCAGGGTAT | CTACTTTGTT | GGCAGAACAT | GGATCTTTGG | 3100 |
| GGTCTGGGGC | CTACAGATCA | GTAGGTGAAT | GGCTAGAAGC | AATCAAAATG | 3150 |
| GGCCGGTACA | CAGAGATTTT | CATGGAAAAT | GGATACAGTT | CAATGGACGC | 3200 |
| TGTGGCTCAG | GTGACCTTGG | AGGATTTGAG | ACGCCTGGGA | GTGACTCTGG | 3250 |
| TCGGTCACCA | GAAGAAGATC | ATGAACAGCC | TTCAAGAGAT | GAAGGTGCAG | 3300 |
| CTGGTAAACG | GGATGGTGCC | AGTGTGACCC | GCACACGGGT | CACTTCTCCA | 3350 |
| AGTGAACAAC | TCTGCACTTT | GTAAACAGCC | CTAAGATTTA | TTTTAACAGA | 3400 |
| GAAAGGGAAA | TGGGTGGTTC | CTAAACCTTT | GAAGGCACTT | GTCTCATCCT | 3450 |
| TTGACTTATA | ATCAACATTT | TACTAAAATC | TCCAGATCTT | CTTCTTAATG | 3500 |
| TCTTCGTTTT | TTTCACTATG | TAAATGTAAC | CTGCGAAGAG | AGCTAACATG | 3550 |
| AGAAACAACA | TCCTATAAAA | ACATAGTAAC | TAAATCTTTC | TCCACTTGCA | 3600 |
| GCCCCTTTCA | AAACTACCAG | GGATCGACTT | GAAAGGAAAA | GTTTAAAGC | 3650 |
| CATGTGTGGG | CAAAGAAACG | CTGCATTTTA | CTGACGTTTA | CTTCGAGTTT | 3700 |
| TATTTGTCTG | CATAAGTGTA | TTGGAGAGCA | ATATGATTAG | ATTATTTCTT | 3750 |
| AAATACAGTT | TGTAATTTAA | AATGGAATTA | CATGTTATAA | GTTATAGAAA | 3800 |
| ATAGTTTACA | GACATGTTGC | CCGGTCAAGG | AAAAGTTCAG | CACAGGGTGT | 3850 |
| ATATTTATTT | TTCTGTGTTA | TATAATTTAC | TTTTAGTTGC | ACTTCTAGAG | 3900 |
| AGTATTAGGC | AATGAATGTG | TATAGACTGT | ATAGTTTGCA | ATATACCGAG | 3950 |
| GAATGGACTT | AAATTGGAAA | TGTATGTATA | TGTGTGTGTA | TGTGCGTATG | 4000 |
| TGTGTGTGTG | TTTGAATATG | TAGATGGTAT | TGTTCTGCTT | GCCTTTTGTA | 4050 |
| TAGGGTTTTA | ATTTTGGCCT | CATACAGCAA | AGGGTGTTCT | AGACTATTTT | 4100 |
| ATGGGTAAGA | GGAATAGGAA | GCCTTAGACC | AAATTTCCCT | CAAGTAGGTG | 4150 |
| TCCTTTCTCT | CATTT | | | | 4165 |

( 2 ) INFORMATION FOR SEQ ID NO:2:

( i ) SEQUENCE CHARACTERISTICS:

(A) LENGTH: 928 amino acids
(B) TYPE: amino acid
(D) TOPOLOGY: linear (xi) SEQUENCE DESCRIPTION: SEQ ID NO:2:

```
Met Arg Gly Ser Gly Pro Arg Gly Ala Gly Arg Arg Arg Thr Gln
 1               5                  10                  15

Gly Arg Gly Gly Gly Gly Asp Thr Pro Arg Val Pro Ala Ser Leu
                20                  25                  30

Ala Gly Cys Tyr Ser Ala Pro Leu Lys Gly Pro Leu Trp Thr Cys
                35                  40                  45

Leu Leu Leu Cys Ala Ala Leu Arg Thr Leu Leu Ala Ser Pro Ser
                50                  55                  60

Asn Glu Val Asn Leu Leu Asp Ser Arg Thr Val Leu Gly Asp Leu
                65                  70                  75

Gly Trp Ile Ala Phe Pro Lys Asn Gly Trp Glu Glu Ile Gly Glu
                80                  85                  90

Val Asp Glu Asn Tyr Pro Pro Ile His Thr Tyr Gln Val Cys Lys
                95                 100                 105

Val Met Glu Gln Asn Gln Asn Asn Trp Leu Leu Thr Ser Trp Ile
               110                 115                 120

Ser Asn Glu Gly Ala Ser Arg Ile Phe Ile Glu Leu Lys Phe Thr
               125                 130                 135

Leu Arg Asp Cys Asn Ser Leu Pro Gly Gly Leu Gly Thr Cys Lys
               140                 145                 150

Glu Thr Phe Asn Met Tyr Tyr Phe Glu Ser Asp Asp Glu Asn Gly
               155                 160                 165

Arg Asn Ile Lys Glu Asn Gln Tyr Ile Lys Ile Asp Thr Ile Ala
               170                 175                 180

Ala Asp Glu Ser Phe Thr Glu Leu Asp Leu Gly Asp Arg Val Met
               185                 190                 195

Lys Leu Asn Thr Glu Val Arg Asp Val Gly Pro Leu Ser Lys Lys
               200                 205                 210

Gly Phe Tyr Leu Ala Phe Gln Asp Val Gly Ala Cys Ile Ala Leu
               215                 220                 225

Val Ser Val Arg Val Tyr Tyr Lys Lys Cys Pro Ser Val Val Arg
               230                 235                 240

His Leu Ala Val Phe Pro Asp Thr Ile Thr Gly Ala Asp Ser Ser
               245                 250                 255

Gln Leu Leu Glu Val Ser Gly Ser Cys Val Asn His Ser Val Thr
               260                 265                 270

Asp Asp Pro Pro Lys Met His Cys Ser Ala Glu Gly Glu Trp Leu
               275                 280                 285

Val Pro Ile Gly Lys Cys Met Cys Lys Ala Gly Tyr Glu Glu Lys
               290                 295                 300

Asn Gly Thr Cys Gln Val Cys Arg Pro Gly Phe Phe Lys Ala Ser
               305                 310                 315

Pro His Ser Gln Thr Cys Ser Lys Cys Pro Pro His Ser Tyr Thr
               320                 325                 330

His Glu Glu Ala Ser Thr Ser Cys Val Cys Glu Lys Asp Tyr Phe
               335                 340                 345

Arg Arg Glu Ser Asp Pro Pro Thr Met Ala Cys Thr Thr Pro Ser
               350                 355                 360

Pro Val Thr Asn Val Lys Lys Gly Lys Ile Ala Lys Asn Ser Ile
               365                 370                 375
```

```
Ser Leu Ser Trp Gln Glu Pro Asp Arg Pro Asn Gly Ile Ile Leu
                380             385                     390

Glu Tyr Glu Ile Lys Tyr Phe Glu Lys Asp Gln Glu Thr Ser Tyr
                395             400                     405

Thr Ile Ile Lys Ser Lys Glu Thr Thr Ile Thr Ala Glu Gly Leu
                410             415                     420

Lys Pro Ala Ser Val Tyr Val Phe Gln Ile Arg Ala Arg Thr Ala
                425             430                     435

Ala Gly Tyr Gly Val Phe Ser Arg Arg Phe Glu Phe Glu Thr Thr
                440             445                     450

Pro Val Ser Val Ala Ala Ser Asn Asp Gln Ser Gln Ile Pro Ile
                455             460                     465

Ile Ala Val Ser Val Thr Val Gly Val Ile Leu Leu Ala Val Met
                470             475                     480

Ile Gly Phe Leu Leu Ser Gly Ser Cys Cys Glu Cys Gly Cys Gly
                485             490                     495

Arg Ala Ser Ser Leu Cys Ala Val Ala His Pro Ser Leu Ile Trp
                500             505                     510

Arg Cys Gly Tyr Ser Lys Ala Lys Gln Asp Pro Glu Glu Glu Lys
                515             520                     525

Met His Phe His Asn Gly His Ile Lys Leu Pro Gly Val Arg Thr
                530             535                     540

Tyr Ile Asp Pro His Thr Tyr Glu Asp Pro Thr Gln Ala Val His
                545             550                     555

Glu Phe Ala Lys Glu Ile Glu Ala Ser Cys Ile Thr Ile Glu Arg
                560             565                     570

Val Ile Gly Ala Gly Glu Phe Gly Glu Val Cys Ser Gly Arg Leu
                575             580                     585

Lys Leu Pro Gly Lys Arg Glu Leu Pro Val Ala Ile Lys Thr Leu
                590             595                     600

Lys Val Gly Tyr Thr Glu Lys Gln Arg Arg Asp Phe Leu Ser Glu
                605             610                     615

Ala Ser Ile Met Gly Gln Phe Asp His Pro Asn Ile Ile His Leu
                620             625                     630

Glu Gly Val Val Thr Lys Ser Lys Pro Val Met Ile Val Thr Glu
                635             640                     645

Tyr Met Glu Asn Gly Ser Leu Asp Thr Phe Leu Lys Lys Asn Asp
                650             655                     660

Gly Gln Phe Thr Val Ile Gln Leu Val Gly Met Leu Arg Gly Ile
                665             670                     675

Ala Ala Gly Met Lys Tyr Leu Ser Asp Met Gly Tyr Val His Arg
                680             685                     690

Asp Leu Ala Ala Arg Asn Ile Leu Ile Asn Ser Asn Leu Val Cys
                695             700                     705

Lys Val Ser Asp Phe Gly Leu Ser Arg Val Leu Glu Asp Asp Pro
                710             715                     720

Glu Ala Ala Tyr Thr Thr Arg Gly Gly Lys Ile Pro Ile Arg Trp
                725             730                     735

Thr Ala Pro Glu Ala Ile Ala Phe Arg Lys Phe Thr Ser Ala Ser
                740             745                     750

Asp Val Trp Ser Tyr Gly Ile Val Met Trp Glu Val Val Ser Tyr
                755             760                     765

Gly Glu Arg Pro Tyr Trp Glu Met Thr Asn Gln Asp Val Ile Lys
```

|     |     |     |     | 770 |     |     |     |     | 775 |     |     |     |     | 780 |
|-----|-----|-----|-----|-----|-----|-----|-----|-----|-----|-----|-----|-----|-----|-----|

Ala Val Glu Glu Gly Tyr Arg Leu Pro Ser Pro Met Asp Cys Pro
                785                     790                     795

Ala Ala Leu Tyr Gln Leu Met Leu Asp Cys Trp Gln Lys Asp Arg
                800                     805                     810

Asn Ser Arg Pro Lys Phe Asp Asp Ile Val Asn Met Leu Asp Lys
                815                     820                     825

Leu Ile Arg Asn Pro Ser Ser Leu Lys Thr Leu Val Asn Ala Ser
                830                     835                     840

Ser Arg Val Ser Thr Leu Leu Ala Glu His Gly Ser Leu Gly Ser
                845                     850                     855

Gly Ala Tyr Arg Ser Val Gly Glu Trp Leu Glu Ala Ile Lys Met
                860                     865                     870

Gly Arg Tyr Thr Glu Ile Phe Met Glu Asn Gly Tyr Ser Ser Met
                875                     880                     885

Asp Ala Val Ala Gln Val Thr Leu Glu Asp Leu Arg Arg Leu Gly
                890                     895                     900

Val Thr Leu Val Gly His Gln Lys Lys Ile Met Asn Ser Leu Gln
                905                     910                     915

Glu Met Lys Val Gln Leu Val Asn Gly Met Val Pro Val
                920                     925         928

(2) INFORMATION FOR SEQ ID NO:3:

(i) SEQUENCE CHARACTERISTICS:
        (A) LENGTH: 1839 bases
        (B) TYPE: nucleic acid
        (C) STRANDEDNESS: single
        (D) TOPOLOGY: linear (xi) SEQUENCE DESCRIPTION: SEQ ID NO:3:

```
ATTCCCCCCC  GCCCTCGCCG  CCGCCACCAC  ACACACGCAC  GCTTCTCTCC          50
ATCTTGTGAT  TCCTTTTTCC  TCCTGAACCC  TCCAGTGGGG  GTGCGAGTTT         100
GTCTTTATCA  CCCCCCATCC  CACCGCCTTC  TTTTCTTCTC  GCTCTCCTAC         150
CCCTCCCCAG  CTTGGTGGGC  GCCTCTTTCC  TTTCTCGCCC  CCTTTCATTT         200
TTATTTATTC  ATATTTATTT  GGCGCCCGCT  CTCTCTCTGT  CCCTTTGCCT         250
GCCTCCCTCC  CTCCGGATCC  CCGCTCTCTC  CCCGGAGTGG  CGCGTCGGGG         300
GCTCCGCCGC  TGGCCAGGCG  TGATGTTGCA  CGTGGAGATG  TTGACGCTGG         350
TGTTTCTGGT  GCTCTGGATG  TGTGTGTTCA  GCCAGGACCC  GGGCTCCAAG         400
GCCGTCGCCG  ACCGCTACGC  TGTCTACTGG  AACAGCAGCA  ACCCCAGATT         450
CCAGAGGGGT  GACTACCATA  TTGATGTCTG  TATCAATGAC  TACCTGGATG         500
TTTTCTGCCC  TCACTATGAG  GACTCCGTCC  AGAAGATAA   GACTGAGCGC         550
TATGTCCTCT  ACATGGTGAA  CTTTGATGGC  TACAGTGCCT  GCGACCACAC         600
TTCCAAAGGG  TTCAAGAGAT  GGAATGTAA   CCGGCCTCAC  TCTCCAAATG         650
GACCGCTGAA  GTTCTCTGAA  AAATTCCAGC  TCTTCACTCC  CTTTTCTCTA         700
GGATTTGAAT  TCAGGCCAGG  CCGAGAATAT  TTCTACATCT  CCTCTGCAAT         750
CCCAGATAAT  GGAAGAAGGT  CCTGTCTAAA  GCTCAAAGTC  TTTGTGAGAC         800
CAACAAATAG  CTGTATGAAA  ACTATAGGTG  TTCATGATCG  TGTTTTCGAT         850
GTTAACGACA  AAGTAGAAAA  TTCATTAGAA  CCAGCAGATG  ACACCGTACA         900
TGAGTCAGCC  GAGCCATCCC  GCGGCGAGAA  CGCGGCACAA  ACACCAAGGA         950
```

| | | | | |
|---|---|---|---|---|
| TACCCAGCCG | CCTTTTGGCA | ATCCTACTGT | TCCTCCTGGC | GATGCTTTTG | 1000 |
| ACATTATAGC | ACAGTCTCCT | CCCATCACTT | GTCACAGAAA | ACATCAGGGT | 1050 |
| CTTGGAACAC | CAGAGATCCA | CCTAACTGCT | CATCCTAAGA | AGGGACTTGT | 1100 |
| TATTGGGTTT | TGGCAGATGT | CAGATTTTGG | TTTTCTTTCT | TTCAGCCTGA | 1150 |
| ATTCTAAGCA | ACAACTTCAG | GTTGGGGGCC | TAAACTTGTT | CCTGCCTCCC | 1200 |
| TCACCCCACC | CCGCCCCACC | CCCAGCCCTG | GCCCTTGGCT | TCTCTCACCC | 1250 |
| CTCCCAAATT | AAATGGACTC | CAGATGAAAA | TGCCAAATTG | TCATAGTGAC | 1300 |
| ACCAGTGGTT | CGTCAGCTCC | TGTGCATTCT | CCTCTAAGAA | CTCACCTCCG | 1350 |
| TTAGCGCACT | GTGTCAGCGG | GCTATGGACA | AGGAAGAATA | GTGGCAGATG | 1400 |
| CAGCCAGCGC | TGGCTAGGGC | TGGGAGGGTT | TTGCTCTCCT | ATGCAATATT | 1450 |
| TATGCCTTCT | CATTCAGAAC | TGTAAGATGA | TCGCGCAGGG | CATCATGTCA | 1500 |
| CCATGTCAGG | TCCGGAGGGG | AGGTATTAAG | AATAGATACG | ATATTACACC | 1550 |
| ATTTCCTATA | GGAGTATGTA | AATGAACAGG | CTTCTAAAAG | GTTGAGACAC | 1600 |
| TGGNTTTTTT | TTTTAATATG | ACTGTCTTAA | AGCATCTTG | ACASCCCAAC | 1650 |
| TTGTGCTCTC | TAAAAGAAGC | CTTTTTTTTT | TTTCTAGGAG | ACAGAGTGGG | 1700 |
| TGTGGAATGC | TAATACAGAG | CAGGTGTGWA | AACAGAGAAA | ACTACAGGTT | 1750 |
| TGCTGGGGGT | GTGTATGTGT | GAGTGCCTCT | AATTTTTTG | GTGACTGGGC | 1800 |
| AGTGCACACC | AGATATTTTT | TCTTTGAATA | CAGATCACG | | 1839 |

( 2 ) INFORMATION FOR SEQ ID NO:4:

( i ) SEQUENCE CHARACTERISTICS:
        ( A ) LENGTH: 228 amino acids
        ( B ) TYPE: amino acid
        ( D ) TOPOLOGY: linear ( x i ) SEQUENCE DESCRIPTION: SEQ ID NO:4:

```
Met Leu His Val Glu Met Leu Thr Leu Val Phe Leu Val Leu Trp
 1               5                  10                  15

Met Cys Val Phe Ser Gln Asp Pro Gly Ser Lys Ala Val Ala Asp
                20                  25                  30

Arg Tyr Ala Val Tyr Trp Asn Ser Ser Asn Pro Arg Phe Gln Arg
                35                  40                  45

Gly Asp Tyr His Ile Asp Val Cys Ile Asn Asp Tyr Leu Asp Val
                50                  55                  60

Phe Cys Pro His Tyr Glu Asp Ser Val Pro Glu Asp Lys Thr Glu
                65                  70                  75

Arg Tyr Val Leu Tyr Met Val Asn Phe Asp Gly Tyr Ser Ala Cys
                80                  85                  90

Asp His Thr Ser Lys Gly Phe Lys Arg Trp Glu Cys Asn Arg Pro
                95                 100                 105

His Ser Pro Asn Gly Pro Leu Lys Phe Ser Glu Lys Phe Gln Leu
               110                 115                 120

Phe Thr Pro Phe Ser Leu Gly Phe Glu Phe Arg Pro Gly Arg Glu
               125                 130                 135

Tyr Phe Tyr Ile Ser Ser Ala Ile Pro Asp Asn Gly Arg Arg Ser
               140                 145                 150

Cys Leu Lys Leu Lys Val Phe Val Arg Pro Thr Asn Ser Cys Met
               155                 160                 165
```

| Lys | Thr | Ile | Gly | Val<br>170 | His | Asp | Arg | Val<br>175 | Phe | Asp | Val | Asn | Asp | Lys<br>180 |
| Val | Glu | Asn | Ser | Leu<br>185 | Glu | Pro | Ala | Asp<br>190 | Thr | Val | His | Glu | Ser<br>195 | |
| Ala | Glu | Pro | Ser | Arg<br>200 | Gly | Glu | Asn | Ala<br>205 | Ala | Gln | Thr | Pro | Arg | Ile<br>210 |
| Pro | Ser | Arg | Leu | Leu<br>215 | Ala | Ile | Leu | Leu<br>220 | Phe | Leu | Leu | Ala | Met | Leu<br>225 |
| Leu | Thr | Leu<br>228 | | | | | | | | | | | | |

( 2 ) INFORMATION FOR SEQ ID NO:5:

( i ) SEQUENCE CHARACTERISTICS:
        ( A ) LENGTH: 37 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCCTCGAGGT CGACCAYMGN GAYYTNGCNR CNMGNAA          37

( 2 ) INFORMATION FOR SEQ ID NO:6:

( i ) SEQUENCE CHARACTERISTICS:
        ( A ) LENGTH: 37 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

CCCTCGAGGT CGACCAYMGN GAYYTNGCNT GYMGNAA          37

( 2 ) INFORMATION FOR SEQ ID NO:7:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( x i ) SEQUENCE DESCRIPTION: SEQ ID NO:7:

CCGCGGTGCG GCCGCCRWAN SHCCANACRT C          31

( 2 ) INFORMATION FOR SEQ ID NO:8:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

TCTGTGACAG ACGATCCTCC C          21

( 2 ) INFORMATION FOR SEQ ID NO:9:

( i ) SEQUENCE CHARACTERISTICS:
        ( A ) LENGTH: 54 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCACGGTGGA CATGTGTGAG TTTTGTCCTG GCTTTGATCA TTAGATGCTG          50

( 2 ) INFORMATION FOR SEQ ID NO:10:

( i ) SEQUENCE CHARACTERISTICS:
        ( A ) LENGTH: 54 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GTTGCAGCAT CTAATGATCA AAGCCAGGAC AAAACTCACA CATGTCCACC          50

GTGC                                                            54
```

( 2 ) INFORMATION FOR SEQ ID NO:11:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
GCACTTGTAC TCCTTGCC                                             18
```

( 2 ) INFORMATION FOR SEQ ID NO:12:

( i ) SEQUENCE CHARACTERISTICS:
        ( A ) LENGTH: 28 amino acids
        ( B ) TYPE: amino acid
        ( D ) TOPOLOGY: linear ( x i ) SEQUENCE DESCRIPTION: SEQ ID NO:12:

```
Asp Arg Tyr Ala Val Tyr Trp Asn Ser Ser Asn Pro Arg Phe Gln
 1               5                  10                   15

Arg Gly Asp Tyr His Asn Asp Val Xaa Asn Asn Asp Tyr
                20              25              28
```

( 2 ) INFORMATION FOR SEQ ID NO:13:

( i ) SEQUENCE CHARACTERISTICS:
        ( A ) LENGTH: 24 amino acids
        ( B ) TYPE: amino acid
        ( D ) TOPOLOGY: linear ( x i ) SEQUENCE DESCRIPTION: SEQ ID NO:13:

```
Met Lys Thr Asn Gly Val His Asp Arg Val Phe Asp Val Asn Asp
 1               5                  10                   15

Lys Val Glu Asn Xaa Leu Glu Pro Ala
                20              24
```

( 2 ) INFORMATION FOR SEQ ID NO:14:

( i ) SEQUENCE CHARACTERISTICS:
        ( A ) LENGTH: 23 amino acids
        ( B ) TYPE: amino acid
        ( D ) TOPOLOGY: linear ( x i ) SEQUENCE DESCRIPTION: SEQ ID NO:14:

```
Val Asn Phe Asp Gly Tyr Ser Ala Xaa Asp His Thr Ser Lys Gly
 1               5                  10                   15

Phe Lys Arg Xaa Glu Xaa Asn Arg
                20          23
```

( 2 ) INFORMATION FOR SEQ ID NO:15:

( i ) SEQUENCE CHARACTERISTICS:
   ( A ) LENGTH: 27 amino acids
   ( B ) TYPE: amino acid
   ( D ) TOPOLOGY: linear ( x i ) SEQUENCE DESCRIPTION: SEQ ID NO:15:

Phe Gln Leu Phe Thr Pro Phe Ser Leu Gly Xaa Glu Xaa Arg Xaa
1               5                   10                  15

Gly Arg Glu Xaa Phe Tyr Asn Ser Xaa Ala Asn Pro
            20                  25      27

( 2 ) INFORMATION FOR SEQ ID NO:16:

( i ) SEQUENCE CHARACTERISTICS:
      ( A ) LENGTH: 8 amino acids
      ( B ) TYPE: amino acid
      ( D ) TOPOLOGY: linear ( x i ) SEQUENCE DESCRIPTION: SEQ ID NO:16:

Lys Arg Trp Glu Cys Asn Arg Pro
1               5               8

( 2 ) INFORMATION FOR SEQ ID NO:17:

( i ) SEQUENCE CHARACTERISTICS:
      ( A ) LENGTH: 37 bases
      ( B ) TYPE: nucleic acid
      ( C ) STRANDEDNESS: single
      ( D ) TOPOLOGY: linear ( x i ) SEQUENCE DESCRIPTION: SEQ ID NO:17:

CCCTCGAGGT CGACGAYMGN TAYGCNGTNT AYTGGAA                                    37

( 2 ) INFORMATION FOR SEQ ID NO:18:

( i ) SEQUENCE CHARACTERISTICS:
      ( A ) LENGTH: 42 bases
      ( B ) TYPE: nucleic acid
      ( C ) STRANDEDNESS: single
      ( D ) TOPOLOGY: linear ( x i ) SEQUENCE DESCRIPTION: SEQ ID NO:18:

CCGCGGTGCG GCCGCTCTAG ARTANCCRTC RAARTTNACC AT                              42

METHODS FOR DETECTING NUCLEIC ACIDS ENCODING AL—1 NEUROTROPHIC FACTOR

This is a continuation of co-pending application Ser. No. 08/330,128 filed on Oct. 27, 1994, which application is incorporated herein by reference and to which application priority is claimed under 35 USC § 120.

FIELD OF THE INVENTION

This application relates to the production of polypeptides involved in neuronal survival and/or growth, in particular the production of purified forms thereof by means of recombinant DNA technology.

BACKGROUND OF THE INVENTION

A number of protein neurotrophic factors, or neurotrophins, have been identified which influence growth and development of the vertebrate nervous system. It is believed that these factors play an important role in promoting the differentiation, survival, and function of diverse groups of neurons in the brain and periphery.

The belief that neurotrophic factors have important signalling functions in neural tissues is based upon the precedent established by work with nerve growth factor (NGF). NGF has been shown, both in vitro and in vivo, to support the survival of sympathetic, sensory, and basal forebrain neurons. Administration of exogenous NGF rescues neurons from cell death during development. Conversely, removal or sequestration of endogenous NGF by administration of anti-NGF antibodies promotes such cell death. Heumann, J. Exp. Biol. 132:133–150 (1987); Hefti, J. Neurosci. 6:2155–2162 (1986); Thoenen and Barde, Annu. Rev. Physiol. 60:284–335 (1980).

Additional neurotrophic factors related to NGF have since been identified. These include brain-derived neurotrophic factor (BDNF) (Leibrock, et al., Nature 341:149–152 (1989)), neurotrophin-3 (NT-3) (Kaisho, et al., FEBS Lett. 266:187 (1990); Maisonpierre, et al., Science 247:1446 (1990); Rosenthal, et al., Neuron 4:767 (1990)), and neurotrophin 4/5 (NT-4/5) (Berkmeier, et al., Neuron 7:857–866 (1991)).

Neurotrophins, similar to other polypeptide growth factors, affect their target cells through interactions with cell surface receptors. According to our current understanding, two kinds of transmembrane glycoproteins act as receptors for the known neurotrophins. Equilibrium binding studies have shown that neurotrophin-responsive neuronal cells possess a common low molecular weight (65,000 –80,000 Daltons), low affinity receptor, typically referred to as $p75^{LNGFR}$ or p75, and high molecular weight (130,000–150,000 Daltons), high and low affinity receptors that are members of the trk family of receptor tyrosine kinases.

Receptor tyrosine kinases are known to serve as receptors for a variety of protein factors that promote cellular proliferation, differentiation, and survival. In addition to the trk receptors, examples of other receptor tyrosine kinases include the receptors for epidermal growth factor (EGF), fibroblast growth factor (FGF), and platelet-derived growth factor (PDGF). Typically, these receptors span the cell membrane, with one portion of the receptor being intracellular and in contact with the cytoplasm, and another portion of the receptor being extracellular. Binding of a ligand to the extracellular portion of the receptor is believed to induce tyrosine kinase activity in the intracellular portion of the receptor, with ensuing phosphorylation of various intracellular proteins involved in cellular signalling pathways.

In addition to receptor tyrosine kinases that serve as receptors for known protein factors, many receptor-like tyrosine kinases have been identified for which no ligand is known. Examples of such "orphan" receptors include recently discovered members of the eph family, which includes eph, elk, cek5, cek7, mek4/cek4/hek, sek, hek2, and bsk (Tuzi, et al., Br. J. Cancer 69:417–421 (1994); Zhou, et al., J. Neurosci. Res. 37:129–143 (1994)). Recently, a protein ligand has been identified for another eph family member, eck (Bartley, et al., Nature 368:558–560(1994)).

Although eph family members are expressed in many different tissues, several family members are expressed in the nervous system or specifically in neurons (Maisonpierre, et al., Oncogene 8:3277–3288 (1993); Lai, et al., Neuron 6:691–704 (1991). In order to better understand the role of these and other orphan receptor tyrosine kinases in the nervous system, it would be useful to identify new ligands that bind to such receptors.

The present invention is based on successful research resulting in the identification, cloning, and sequencing of an eph-related tyrosine kinase receptor, referred to as REK7, and its ligand, referred to as AL-1.

It is an object of the present invention to provide nucleic acid encoding AL-1, and to use the nucleic acid to produce AL-1 in recombinant host cells for diagnostic use or for therapeutic use.

It is another object to use such nucleic acids encoding AL-1, and portions thereof, to identify related nucleic acids in the cells or tissues of various animal species.

It is another object to provide derivatives and modified forms of AL-1, including amino acid sequence variants and covalent derivatives thereof, as well as antagonists of AL-1.

It is another object to prepare immunogens for raising antibodies, as well as to obtain antibodies, capable of binding to AL-1, or derivatives or modified forms thereof.

These and other objects of the invention will be apparent to the ordinary artisan upon consideration of the specification as a whole.

SUMMARY OF THE INVENTION

These objects are accomplished by first providing isolated DNA comprising the nucleotide coding sequence for AL-1, an expression vector comprising the nucleotide coding sequence for AL-1, host cells transformed with the vector, including mammalian and bacterial host cells, and a method of using a nucleic acid molecule encoding AL-1 to effect the production of AL-1, comprising culturing a host cell transfected to express such nucleic acid molecule and recovering AL-1 from the host cell culture. In this method, preferably the host cell is transfected with an expression vector comprising the nucleotide coding sequence for AL-1.

By providing the full nucleotide coding sequence for AL-1, the invention enables the production of AL-1 by means of recombinant DNA technology, thereby making available for the first time sufficient quantities of substantially pure AL-1 protein for diagnostic and therapeutic uses with a variety of neurological disorders. In a preferred embodiment, the invention provides AL-1 that is free of other human proteins.

Modified and variant forms of AL-1 are produced in vitro by means of chemical or enzymatic treatment or in vivo by means of recombinant DNA technology. Such polypeptides differ from native AL-1, for example, by virtue of one or more amino acid substitutions, deletions or insertions, or in the extent or pattern of glycosylation, but substantially retain a biological activity of native AL-1.

Antibodies to AL-1 are produced by immunizing an animal with AL-1 or a fragment thereof, optionally in conjunction with an immunogenic polypeptide, and thereafter recovering antibodies from the serum of the immunized animals. Alternatively, monoclonal antibodies are prepared from cells of the immunized animal in conventional fashion. Antibodies obtained by routine screening will bind to AL-1 but will not substantially bind to (i.e., cross react with) NGF, BDNF, NT-3, NT-4/5, or other neurotrophic factors. Immobilized anti-AL-1 antibodies are particularly useful in the detection of AL-1 in clinical samples for diagnostic purposes, and in the purification of AL-1.

AL-1, its derivatives, or its antibodies are formulated with physiologically acceptable carriers, especially for therapeutic use. Such carriers are used, for example, to provide sustained-release formulations of AL-1.

In further aspects, the invention provides a method for determining the presence of a nucleic acid molecule encoding AL-1 in test samples prepared from cells, tissues, or biological fluids, comprising contacting the test sample with isolated DNA comprising all or a portion of the nucleotide coding sequence for AL-1 and determining whether the isolated DNA hybridizes to a nucleic acid molecule in the test sample. DNA comprising all or a portion of the nucleotide coding sequence for AL-1 is also used in hybridization assays to identify and to isolate nucleic acids sharing substantial sequence identity to the coding sequence for AL-1, such as nucleic acids that encode allelic variants of AL-1.

Also provided is a method for amplifying a nucleic acid molecule encoding AL-1 that is present in a test sample, comprising the use of an oligonucleotide having a portion of the nucleotide coding sequence for AL-1 as a primer in a polymerase chain reaction.

BRIEF DESCRIPTION OF THE DRAWINGS

FIG. I shows the nucleotide coding sequence (SEQ. ID. NO: 1), and the deduced amino acid sequence (SEQ. ID. NO: 2) encoded by the isolated REK7 cDNA. The N-terminus of the mature REK7 protein is indicated by a rightward arrow and the C-terminus of the REK7 extracellular domain is indicated by a vertical arrow.

FIG. 2 shows the nucleotide coding sequence (SEQ. ID. NO: 3), and the deduced amino acid sequence (SEQ. ID. NO: 4) encoded by the isolated AL-1 cDNA. The N-terminus of the mature AL-1 protein is indicated by a rightward arrow (the mature protein begins with amino acid residue number 21). The underlined sequences corresponds to the sequences obtained by sequencing of purified BT20 cell-derived AL-1. The shaded boxes indicate potential N-glycosylation sites. The unshaded box shows the C-terminal hydrophobic domain and the upward arrow indicates a potential attachment site for glycophosphatidyl-inositol (GPI).

DETAILED DESCRIPTION OF THE PREFERRED EMBODIMENTS

"AL-1" or "AL-1 protein" refers to a polypeptide or protein encoded by the AL-1 nucleotide sequence set forth in FIG. 2; a polypeptide that is the translated amino acid sequence set forth in FIG. 2; fragments thereof having greater than about 5 amino acid residues and comprising an immune epitope or other biologically active site of AL-1; amino acid sequence variants of the amino acid sequence set forth in FIG. 2 wherein one or more amino acid residues are added at the N- or C-terminus of, or within, said FIG 2 sequence or its fragments as defined above; amino acid sequence variants of said FIG. 2 sequence or its fragments as defined above wherein one or more amino acid residues of said FIG. 2 sequence or fragment thereof are deleted, and optionally substituted by one or more amino acid residues; and derivatives of the above proteins, polypeptides, or fragments thereof, wherein an amino acid residue has been covalently modified so that the resulting product is a non-naturally occurring amino acid. AL-1 amino acid sequence variants may be made synthetically, for example, by site-directed or PCR mutagenesis, or may exist naturally, as in the case of allelic forms and other naturally occurring variants of the translated amino acid sequence set forth in FIG. 2 that may occur in human and other animal species. In any event, such fragments, variants, and derivatives exclude any polypeptide heretofore identified, including any known neurotrophic factor, such as nerve growth factor (NGF), brain derived neurotrophic factor (BDNF), neurotrophin-3 (NT-3), and neurotrophin-4/5 (NT-4/5), as well as statutorily obvious variants thereof.

A AL-1 amino acid sequence variant is included within the scope of the invention provided that it is functionally active. As used herein, "functionally active" and "functional activity" in reference to AL-1 means that the AL-1 is able to promote the growth, survival, and/or differentiation of neurons, especially axon fasciculation, whether the neurons be central, peripheral, or motorneurons, and/or that the AL-1 is immunologically cross-reactive with an antibody directed against an epitope of naturally occurring AL-1. Therefore, AL-1 amino acid sequence variants generally will share at least about 75% (preferably greater than 80% and more preferably greater than 90%) sequence identity with the translated amino acid sequence set forth in FIG. 2, after aligning the sequences to provide for maximum homology, as determined, for example, by the Fitch, et al., Proc. Nat. Acad. Sci. USA 80:1382–1386 (1983), version of the algorithm described by Needleman, et al., J. Mol. Biol. 48:443–453 (1970).

Amino acid sequence variants of AL-1 are prepared by introducing appropriate nucleotide changes into AL-1 DNA and thereafter expressing the resulting modified DNA in a host cell, or by in vitro synthesis. Such variants include, for example, deletions from, or insertions or substitutions of, amino acid residues within the AL-1 amino acid sequence set forth in FIG. 2. Any combination of deletion, insertion, and substitution may be made to arrive at an amino acid sequence variant of AL-1, provided that such variant possesses the desired characteristics described herein. Changes that are made in the amino acid sequence set forth in FIG. 2 to arrive at an amino acid sequence variant of AL-1 also may result in further modifications of AL-1 upon its expression in host cells, for example, by virtue of such changes introducing or moving sites of glycosylation, or introducing membrane anchor sequences as described, for example, in PCT Pat. Pub. No. WO 89/01041 (published Feb. 9, 1989).

There are two principal variables in the construction of amino acid sequence variants of AL-1: the location of the mutation site and the nature of the mutation. These are variants from the amino acid sequence set forth in FIG. 2, and may represent naturally occurring allelic forms of AL-1, or predetermined mutant forms of AL-1 made by mutating AL-1 DNA, either to arrive at an allele or a variant not found in nature. In general, the location and nature of the mutation chosen will depend upon the AL-1 characteristic to be modified.

For example, due to the degeneracy of nucleotide coding sequences, mutations can be made in the AL-1 nucleotide sequence set forth in FIG. 2 without affecting the amino acid sequence of the AL-1 encoded thereby. Other mutations can be made that will result in a AL-1 that has an amino acid sequence different from that set forth in FIG. 2, but which is functionally active. Such functionally active amino acid sequence variants of AL-1 are selected, for example, by substituting one or more amino acid residues in the amino acid sequence set forth in FIG. 2 with other amino acid residues of a similar or different polarity or charge.

One useful approach is called "alanine scanning mutagenesis." Here, a an amino acid residue or group of target residues are identified (e.g., charged residues such as arg, asp, his, lys, and glu) and, by means of recombinant DNA technology, replaced by a neutral or negatively charged amino acid (most preferably alanine or polyalanine) to affect the interaction of the amino acids with the surrounding aqueous environment in or outside the cell. Cunningham, et al., Science 244: 1081–1085 (1989). Those domains demonstrating functional sensitivity to the substitutions then are refined by introducing further or other variants at or for the sites of substitution.

Obviously, such variations that, for example, convert the amino acid sequence set forth in FIG. 2 to the amino acid sequence of a known neurotrophic factor, such as NGF, BDNF, NT-3, NT-4/5, or another known polypeptide or protein are not included within the scope of this invention, nor are any other fragments, variants, and derivatives of the amino acid AL-1 that are not novel and unobvious over the prior art. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed AL-1 variants are screened for functional activity.

Amino acid sequence deletions generally range from about 1 to 30 residues, more preferably about 1 to 10 residues, and typically are contiguous. Deletions from regions of substantial homology with other tyrosine kinase receptor ligands, for example, are more likely to affect the functional activity of AL-1. Generally, the number of consecutive deletions will be selected so as to preserve the tertiary structure of AL-1 in the affected domain, e.g., beta-pleated sheet or alpha helix.

Amino acid sequence insertions include amino- and/or carboxyl-terminal fusions ranging in length from one amino acid residue to polypeptides containing a hundred or more residues, as well as intrasequence insertions of single or multiple amino acid residues. Intrasequence insertions (i.e., insertions made within the amino acid sequence set forth in FIG. 2) may range generally from about 1 to 10 residues, more preferably 1 to 5, most preferably 1 to 3. Examples of terminal insertions include AL-1 with an N-terminal methionyl residue (such as may result from the direct expression of AL-1 in recombinant cell culture), and AL-1 with a heterologous N-terminal signal sequence to improve the secretion of AL-1 from recombinant host cells. Such signal sequences generally will be homologous to the host cell used for expression of AL-1, and include STII or lpp for *E. coli*, alpha factor for yeast, and viral signals such as herpes gD for mammalian cells. Other insertions include the fusion to the N- or C-terminus of AL-1 of immunogenic polypeptides (for example, bacterial polypeptides such as beta-lactamase or an enzyme encoded by the *E. coli* trp locus, or yeast protein), and C-terminal fusions with proteins having a long half-life such as immunoglobulin constant regions, albumin, or ferritin, as described in PCT Pat. Pub. No WO 89/02922 (published Apr. 6, 1989).

The third group of variants are those in which at least one amino acid residue in the amino acid sequence set forth in FIG. 2, and preferably only one, has been removed and a different residue inserted in its place. The sites of greatest interest for making such substitutions are in the regions of the amino acid sequence set forth in FIG. 2 that have the greatest homology with other tyrosine kinase receptor ligands. Those sites are likely to be important to the functional activity of the AL-1. Accordingly, to retain functional activity, those sites, especially those falling within a sequence of at least three other identically conserved sites, are substituted in a relatively conservative manner. Such conservative substitutions are shown in Table 1 under the heading of preferred substitutions. If such substitutions do not result in a change in functional activity, then more substantial changes, denominated exemplary substitutions in Table 1, or as further described below in reference to amino acid classes, may be introduced and the resulting variant AL-1 analyzed for functional activity.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Insertional, deletional, and substitutional changes in the amino acid sequence set forth in FIG. 2 may be made to improve the stability of AL-1. For example, trypsin or other protease cleavage sites are identified by inspection of the encoded amino acid sequence for an arginyl or lysinyl residue. These are rendered inactive to protease by substituting the residue with another residue, preferably a basic residue such as glutamine or a hydrophobic residue such as serine; by deleting the residue; or by inserting a prolyl residue immediately after the residue. Also, any cysteine residues not involved in maintaining the proper conformation of AL-1 for functional activity may be substituted, generally with serine, to improve the oxidative stability of the molecule and prevent aberrant crosslinking.

Covalent modifications of AL-1 molecules also are included within the scope of this invention. For example, covalent modifications are introduced into AL-1 by reacting targeted amino acid residues of the AL-1 with an organic derivatizing agent that is capable of reacting with selected amino acid side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, αbromo-β-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking AL-1 to a water-insoluble support matrix or surface for use in the method for purifying anti-AL-1 antibodies, or for therapeutic use. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group. Creighton, *Proteins: Structure and Molecular Properties*, pp.79–86 (W. H. Freeman & Co., 1983). AL-1 also is covalently linked to nonproteinaceous polymers, e.g. polyethylene glycol, polypropylene glycol or polyoxyalkylenes, in the manner set forth in U.S. Pat. Nos. 4,179,337; 4,301,144; 4,496,689; 4,640,835; 4,670,417; or 4,791,192.

"AL-1 antagonist" or "antagonist" refers to a substance that opposes or interferes with a functional activity of AL-1.

"Cell," "host cell," "cell line," and "cell culture" are used interchangeably and all such terms should be understood to include progeny. Thus, the words "transformants" and "transformed cells" include the primary subject cell and cultures derived therefrom without regard for the number of times the cultures have been passaged. It should also be understood that all progeny may not be precisely identical in DNA content, due to deliberate or inadvertent mutations. "Plasmids" are DNA molecules that are capable of replicating within a host cell, either extrachromosomally or as part of the host cell chromosome(s), and are designated by a lower case "p" preceded and/or followed by capital letters and/or numbers. The starting plasmids herein are commercially available, are publicly available on an unrestricted basis, or can be constructed from such available plasmids as disclosed herein and/or in accordance with published procedures. In certain instances, as will be apparent to the ordinarily skilled artisan, other plasmids known in the art may be used interchangeably with plasmids described herein.

"Control sequences" refers to DNA sequences necessary for the expression of an operably linked nucleotide coding sequence in a particular host cell. The control sequences that are suitable for expression in prokaryotes, for example, include origins of replication, promoters, ribosome binding sites, and transcription termination sites. The control sequences that are suitable for expression in eukaryotes, for example, include origins of replication, promoters, ribosome binding sites, polyadenylation signals, and enhancers.

An "exogenous" element is one that is foreign to the host cell, or homologous to the host cell but in a position within the host cell in which the element is ordinarily not found.

"Digestion" of DNA refers to the catalytic cleavage of DNA with an enzyme that acts only at certain locations in the DNA. Such enzymes are called restriction enzymes or restriction endonucleases, and the sites within DNA where such enzymes cleave are called restriction sites. If there are multiple restriction sites within the DNA, digestion will produce two or more linearized DNA fragments (restriction fragments). The various restriction enzymes used herein are commercially available and their reaction conditions, cofactors, and other requirements as established by the enzyme manufacturers are used. Restriction enzymes commonly are designated by abbreviations composed of a capital letter followed by other letters representing the microorganism from which each restriction enzyme originally was obtained and then a number designating the particular enzyme. In general, about 1 μg of DNA is digested with about 1–2 units of enzyme in about 20 μl of buffer solution.

Appropriate buffers and substrate amounts for particular restriction enzymes are specified by the manufacturer, and/or are well known in the art.

"Recovery" or "isolation" of a given fragment of DNA from a restriction digest typically is accomplished by separating the digestion products, which are referred to as "restriction fragments," on a polyacrylamide or agarose gel by electrophoresis, identifying the fragment of interest on the basis of its mobility relative to that of marker DNA fragments of known molecular weight, excising the portion of the gel that contains the desired fragment, and separating the DNA from the gel, for example by electroelution.

"Ligation" refers to the process of forming phosphodiester bonds between two double-stranded DNA fragments. Unless otherwise specified, ligation is accomplished using known buffers and conditions with 10 units of T4 DNA ligase per 0.5 µg of approximately equimolar amounts of the DNA fragments to be ligated.

"Oligonucleotides" are short-length, single- or double-stranded polydeoxynucleotides that are chemically synthesized by known methods (involving, for example, triester, phosphoramidite, or phosphonate chemistry), such as described by Engels, et al., Agnew. Chem. Int. Ed. Engl. 28:716–734 (1989). They are then purified, for example, by polyacrylamide gel electrophoresis.

"Polymerase chain reaction," or "PCR," as used herein generally refers to a method for amplification of a desired nucleotide sequence in vitro, as described in U.S. Pat. No. 4,683,195. In general, the PCR method involves repeated cycles of primer extension synthesis, using two oligonucleotide primers capable of hybridizing preferentially to a template nucleic acid. Typically, the primers used in the PCR method will be complementary to nucleotide sequences within the template at both ends of or flanking the nucleotide sequence to be amplified, although primers complementary to the nucleotide sequence to be amplified also may be used. Wang, et al., in *PCR Protocols*, pp.70–75 (Academic Press, 1990); Ochman, et al., in *PCR Protocols*, pp. 219–227; Triglia, et al., Nuc. Acids Res. 16:8186 (1988).

"PCR cloning" refers to the use of the PCR method to amplify a specific desired nucleotide sequence that is present amongst the nucleic acids from a suitable cell or tissue source, including total genomic DNA and cDNA transcribed from total cellular RNA. Frohman, et al., Proc. Nat. Acad. Sci. USA 85:8998–9002 (1988); Saiki, et al., Science 239:487–492 (1988); Mullis, et al., Meth. Enzymol. 155:335–350 (1987).

"Stringent conditions" for hybridization or annealing of nucleic acid molecules are those that (1) employ low ionic strength and high temperature for washing, for example, 0.015M NaCl/0.0015M sodium citrate/0.1% sodium dodecyl sulfate (SDS) at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC and 0.1% SDS.

"AL-1 nucleic acid" is RNA or DNA that encodes AL-1. "AL-1 DNA" is DNA that encodes AL-1. AL-1 DNA is obtained from CDNA or genomic DNA libraries, or by in vitro synthesis. Identification of AL-1 DNA within a CDNA or a genomic DNA library, or in some other mixture of various DNAs, is conveniently accomplished by the use of an oligonucleotide hybridization probe that is labeled with a detectable moiety, such as a radioisotope. Keller, et al., *DNA Probes*, pp.149–213 (Stockton Press, 1989). To identify DNA encoding AL-1, the nucleotide sequence of the hybridization probe preferably is selected so that the hybridization probe is capable of hybridizing preferentially to DNA encoding the AL-1 amino acid sequence set forth in FIG. 2, or a variant or derivative thereof as described herein, under the hybridization conditions chosen. Another method for obtaining AL-1 nucleic acid is to chemically synthesize it using one of the methods described, for example, by Engels, et al., Agnew. Chem. Int. Ed. Engl. 28:716–734 (1989).

If the entire nucleotide coding sequence for AL-1 is not obtained in a single cDNA, genomic DNA, or other DNA, as determined, for example, by DNA sequencing or restriction endonuclease analysis, then appropriate DNA fragments (e.g., restriction fragments or PCR amplification products) may be recovered from several DNAs and covalently joined to one another to construct the entire coding sequence. The preferred means of covalently joining DNA fragments is by ligation using a DNA ligase enzyme, such as T4 DNA ligase.

"Isolated" AL-1 nucleic acid is AL-1 nucleic acid that is identified and separated from (or otherwise substantially free from), contaminant nucleic acid encoding other polypeptides. The isolated AL-1 nucleic acid can be incorporated into a plasmid or expression vector, or can be labeled for diagnostic and probe purposes, using a label as described further herein in the discussion of diagnostic assays and nucleic acid hybridization methods.

For example, isolated AL-1 DNA, or a fragment thereof comprising at least about 15 nucleotides, is used as a hybridization probe to detect, diagnose, or monitor disorders or diseases that involve changes in AL-1 expression, such as may result from neuron damage. In one embodiment of the invention, total RNA in a tissue sample from a patient (that is, a human or other mammal) can be assayed for the presence of AL-1 messenger RNA, wherein the decrease in the amount of AL-1 messenger RNA is indicative of neuronal degeneration.

Isolated AL-1 nucleic acid also is used to produce AL-1 by recombinant DNA and recombinant cell culture methods. In various embodiments of the invention, host cells are transformed or transfected with recombinant DNA molecules comprising an isolated AL-1 DNA, to obtain expression of the AL-1 DNA and thus the production of AL-1 in large quantities. DNA encoding amino acid sequence variants of AL-1 is prepared by a variety of methods known in the art. These methods include, but are not limited to, isolation from a natural source (in the case of naturally occurring amino acid sequence variants of AL-1) or preparation by site-directed (or oligonucleotide-mediated) mutagenesis, PCR mutagenesis, and cassette mutagenesis of an earlier prepared DNA encoding a variant or a non-variant form of AL-1.

Site-directed mutagenesis is a preferred method for preparing substitution, deletion, and insertion variants of AL-1 DNA. This technique is well known in the art, Zoller, et al., Meth. Enz. 100:4668–500 (1983); Zoller, et al., Meth. Enz. 154:329–350 (1987); Carter, Meth. Enz. 154:382–403 (1987); Horwitz, et al., Meth. Enz. 185:599–611 (1990), and has been used, for example, to produce amino acid sequence variants of trypsin and T4 lysozyme, which variants have certain desired functional properties. Perry, et al., Science 226:555–557 (1984); Craik, et al., Science 228:291–297 (1985).

Briefly, in carrying out site-directed mutagenesis of AL-1 DNA, the AL-1 DNA is altered by first hybridizing an oligonucleotide encoding the desired mutation to a single strand of such AL-1 DNA. After hybridization, a DNA polymerase is used to synthesize an entire second strand, using the hybridized oligonucleotide as a primer, and using the single strand of AL-1 DNA as a template. Thus, the oligonucleotide encoding the desired mutation is incorporated in the resulting double-stranded DNA.

Oligonucleotides for use as hybridization probes or primers may be prepared by any suitable method, such as by purification of a naturally occurring DNA or by in vitro synthesis. For example, oligonucleotides are readily synthesized using various techniques in organic chemistry, such as described by Narang, et al., Meth. Enzymol. 68:90–98 (1979); Brown, et al., Meth. Enzymol. 68:109–151 (1979); Caruther, et al., Meth. Enzymol. 154:287–313 (1985). The general approach to selecting a suitable hybridization probe or primer is well known. Keller, et al., *DNA Probes*, pp.11–18 (Stockton Press, 1989). Typically, the hybridization probe or primer will contain 10–25 or more nucleotides, and will include at least 5 nucleotides on either side of the sequence encoding the desired mutation so as to ensure that the oligonucleotide will hybridize preferentially to the single-stranded DNA template molecule.

Multiple mutations are introduced into AL-1 DNA to produce amino acid sequence variants of AL-1 comprising several or a combination of insertions, deletions, or substitutions of amino acid residues as compared to the amino acid sequence set forth in FIG. 2. If the sites to be mutated are located close together, the mutations may be introduced simultaneously using a single oligonucleotide that encodes all of the desired mutations. If, however, the sites to be mutated are located some distance from each other (separated by more than about ten nucleotides), it is more difficult to generate a single oligonucleotide that encodes all of the desired changes. Instead, one of two alternative methods may be employed.

In the first method, a separate oligonucleotide is generated for each desired mutation. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for introducing a single mutation: a single strand of a previously prepared AL-1 DNA is used as a template, an oligonucleotide encoding the first desired mutation is annealed to this template, and a heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid sequence variants of AL-1. Higuchi, in *PCR Protocols*, pp.177–183 (Academic Press, 1990); Vallette, et al., Nuc. Acids Res. 17:723–733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, for example, one of the primers is designed to overlap the position of the mutation and to contain the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. Wagner, et al., in *PCR Topics*, pp.69–71 (Springer-Verlag, 1991).

If the ratio of template to product amplified DNA is extremely low, the majority of product DNA fragments incorporate the desired mutation(s). This product DNA is used to replace the corresponding region in the plasmid that served as PCR template using standard recombinant DNA methods. Mutations at separate positions can be introduced simultaneously by either using a mutant second primer, or performing a second PCR with different mutant primers and ligating the two resulting PCR fragments simultaneously to the plasmid fragment in a three (or more)-part ligation.

Another method for preparing variants, cassette mutagenesis, is based on the technique described by Wells et al., Gene, 34:315–323 (1985). The starting material is the plasmid (or other vector) comprising the AL-1 DNA to be mutated. The codon(s) in the AL-1 DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the AL-1 DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated AL-1 DNA sequence.

AL-1 DNA, whether cDNA or genomic DNA or a product of in vitro synthesis, is ligated into a replicable vector for further cloning or for expression. "Vectors" are plasmids and other DNAs that are capable of replicating autonomously within a host cell, and as such, are useful for performing two functions in conjunction with compatible host cells (a vector-host system). One function is to facilitate the cloning of the nucleic acid that encodes the AL-1, i.e., to produce usable quantities of the nucleic acid. The other function is to direct the expression of AL-1. One or both of these functions are performed by the vector-host system. The vectors will contain different components depending upon the function they are to perform as well as the host cell with which they are to be used for cloning or expression.

To produce AL-1, an expression vector will contain nucleic acid that encodes AL-1 as described above. The AL-1 of this invention is expressed directly in recombinant cell culture, or as a fusion with a heterologous polypeptide, preferably a signal sequence or other polypeptide having a specific cleavage site at the junction between the heterologous polypeptide and the AL-1.

In one example of recombinant host cell expression, mammalian cells are transfected with an expression vector comprising AL-1 DNA and the AL-1 encoded thereby is recovered from the culture medium in which the recombinant host cells are grown. But the expression vectors and methods disclosed herein are suitable for use over a wide range of prokaryotic and eukaryotic organisms.

Prokaryotes may be used for the initial cloning of DNAs and the construction of the vectors useful in the invention. However, prokaryotes may also be used for expression of DNA encoding AL-1. Polypeptides that are produced in prokaryotic host cells typically will be non-glycosylated.

Plasmid or viral vectors containing replication origins and other control sequences that are derived from species compatible with the host cell are used in connection with prokaryotic host cells, for cloning or expression of an isolated DNA. For example, E. coli typically is transformed using pBR322, a plasmid derived from an E. coli species. Bolivar, et al., Gene 2:95–113 (1987). PBR322 contains genes for ampicillin and tetracycline resistance so that cells transformed by the plasmid can easily be identified or selected. For it to serve as an expression vector, the pBR322 plasmid, or other plasmid or viral vector, must also contain, or be modified to contain, a promoter that functions in the host cell to provide messenger RNA (MRNA) transcripts of a DNA inserted downstream of the promoter. Rangagwala, et al., Bio/Technology 9:477–479 (1991).

In addition to prokaryotes, eukaryotic microbes, such as yeast, may also be used as hosts for the cloning or expression of DNAs useful in the invention. Saccharomyces cerevisiae, or common baker's yeast, is the most commonly used eukaryotic microorganism. Plasmids useful for cloning or expression in yeast cells of a desired DNA are well known, as are various promoters that function in yeast cells to produce mRNA transcripts.

Furthermore, cells derived from multicellular organisms also may be used as hosts for the cloning or expression of DNAs useful in the invention. Mammalian cells are most commonly used, and the procedures for maintaining or propagating such cells in vitro, which procedures are commonly referred to as tissue culture, are well known. Kruse & Patterson, eds., Tissue Culture (Academic Press, 1977). Examples of useful mammalian cells are human cell lines such as 293, HeLa, and WI-38, monkey cell lines such as COS-7 and VERO, and hamster cell lines such as BHK-21 and CHO, all of which are publicly available from the American Type Culture Collection (ATCC), Rockville, Md. 20852 USA.

Expression vectors, unlike cloning vectors, should contain a promoter that is recognized by the host organism and is operably linked to the AL-1 nucleic acid. Promoters are untranslated sequences that are located upstream from the start codon of a gene and that control transcription of the gene (that is, the synthesis of mRNA). Promoters typically fall into two classes, inducible and constitutive. Inducible promoters are promoters that initiate high level transcription of the DNA under their control in response to some change in culture conditions, for example, the presence or absence of a nutrient or a change in temperature.

A large number of promoters are known, that may be operably linked to AL-1 DNA to achieve expression of AL-1 in a host cell. This is not to say that the promoter associated with naturally occurring AL-1 DNA is not usable. However, heterologous promoters generally will result in greater transcription and higher yields of expressed AL-1.

Promoters suitable for use with prokaryotic hosts include the β-lactamase and lactose promoters, Goeddel, et al., Nature 281:544–548 (1979), tryptophan (trp) promoter, Goeddel, et al., Nuc. Acids Res. 8:4057–4074 (1980), and hybrid promoters such as the tac promoter, deBoer, et al., Proc. Natl. Acad. Sci. USA 80:21–25 (1983). However, other known bacterial promoters are suitable. Their nucleotide sequences have been published, Siebenlist, et al., Cell 20:269–281 (1980), thereby enabling a skilled worker operably to ligate them to DNA encoding AL-1 using linkers or adaptors to supply any required restriction sites. Wu, et al., Meth. Enz. 152:343–349 (1987).

Suitable promoters for use with yeast hosts include the promoters for 3-phosphoglycerate kinase, Hitzeman, et al., J. Biol. Chem. 255:12073–12080 (1980); Kingsman, et al., Meth. Enz. 185:329–341 (1990), or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Dodson, et al., Nuc. Acids res. 10:2625–2637 (1982); Emr, Meth. Enz. 185:231–279 (1990).

Expression vectors useful in mammalian cells typically include a promoter derived from a virus. For example, promoters derived from polyoma virus, adenovirus, cytomegalovirus (CMV), and simian virus 40 (SV40) are commonly used. Further, it is also possible, and often desirable, to utilize promoter or other control sequences associated with a naturally occurring DNA that encodes AL-1, provided that such control sequences are functional in the particular host cell used for recombinant DNA expression.

Other control sequences that are desirable in an expression vector in addition to a promoter are a ribosome binding site, and in the case of an expression vector used with eukaryotic host cells, an enhancer. Enhancers are cis-acting elements of DNA, usually about from 10–300 bp, that act on a promoter to increase the level of transcription. Many enhancer sequences are now known from mammalian genes (for example, the genes for globin, elastase, albumin, α-fetoprotein and insulin). Typically, however, the enhancer used will be one from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. Kriegler, Meth. Enz. 185:512–527 (1990).

Expression vectors may also contain sequences necessary for the termination of transcription and for stabilizing the messenger RNA (mRNA). Balbas, et al., Meth. Enz. 185:14–37 (1990); Levinson, Meth. Enz. 185:485–511 (1990). In the case of expression vectors used with eukaryotic host cells, such transcription termination sequences may be obtained from the untranslated regions of eukaryotic or viral DNAs or cDNAs. These regions contain polyadenylation sites as well as transcription termination sites. Birnsteil, et al., Cell 41:349–359 (1985).

In general, control sequences are DNA sequences necessary for the expression of an operably liked coding sequence in a particular host cell. "Expression" refers to transcription and/or translation. "Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

Expression and cloning vectors also will contain a sequence that enables the vector to replicate in one or more selected host cells. Generally, in cloning vectors this sequence is one that enables the vector to replicate independently of the host chromosome(s), and includes origins of replication or autonomously replicating sequences. Such sequences are well known for a variety of bacteria, yeast, and viruses. The origin of replication from the plasmid pBR322 is suitable for most gram-negative bacteria, the 2 μ plasmid origin is suitable for yeast, and various viral origins (for example, from SV40, polyoma, or adenovirus) are useful for cloning vectors in mammalian cells. Most expression vectors are "shuttle" vectors, i.e. they are capable of replication in at least one class of organisms but can be transfected into another organism for expression. For example, a vector may be cloned in $E. coli$ and then the same vector is transfected into yeast or mammalian cells for expression even though it is not capable of replicating independently of the host cell chromosome.

The expression vector may also include an amplifiable gene, such as that comprising the coding sequence for dihydrofolate reductase (DHFR). Cells containing an expression vector that includes a DHFR gene may be cultured in the presence of methotrexate, a competitive antagonist of DHFR. This leads to the synthesis of multiple copies of the DHFR gene and, concomitantly, multiple copies of other DNA sequences comprising the expression vector. Ringold, et al., J. Mol. Apl. Genet., 1:165–175 (1981), such as a DNA sequence encoding AL-1. In that manner, the level of AL-1 produced by the cells may be increased.

DHFR protein encoded by the expression vector also may be used as a selectable marker of successful transfection. For example, if the host cell prior to transformation is lacking in DHFR activity, successful transformation by an expression vector comprising DNA sequences encoding AL-1 and DHFR protein can be determined by cell growth in medium containing methotrexate. Also, mammalian cells transformed by an expression vector comprising DNA sequences encoding AL-1, DHFR protein, and aminoglycoside 3' phosphotransferase (APH) can be determined by cell growth in medium containing an aminoglycoside antibiotic such as kanamycin or neomycin. Because eukaryotic cells do not normally express an endogenous APH activity, genes encoding APH protein, commonly referred to as neo$^r$ genes, may be used as dominant selectable markers in a wide range of eukaryotic host cells, by which cells transfected by the vector can easily be identified or selected. Jiminez, et al., Nature, 287:869–871 (1980); Colbere-Garapin, et al., J. Mol. Biol. 150:1–14 (1981); Okayama & Berg, Mol. Cell. Biol., 3:280–289 (1983).

Many other selectable markers are known that may be used for identifying and isolating recombinant host cells that express AL-1. For example, a suitable selection marker for use in yeast is the trp1 gene present in the yeast plasmid YRp7. Stinchcomb, et al., Nature 282:39–43 (1979); Kingsman, et al., Gene 7:141–152 (1979); Tschemper, et al., Gene 10:157–166 (1980). The trp1 gene provides a selection marker for a mutant strain of yeast lacking the ability to grow in tryptophan, for example, ATCC No. 44076 or PEP4-1 (available from the American Type Culture Collection, Rockville, Md. 20852 USA). Jones, Genetics 85:12 (1977). The presence of the trp1 lesion in the yeast host cell genome then provides an effective environment for detecting transformation by growth in the absence of tryptophan. Similarly, Leu2-deficient yeast strains (ATCC Nos. 20622 or 38626) are complemented by known plasmids bearing the Leu2 gene.

Particularly useful in the invention are expression vectors that provide for the transient expression in mammalian cells of DNA encoding AL-1. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Yang, et al., Cell 47:3–10 (1986); Wong, et al., Science 228:810–815 (1985); Lee, et al., Proc. Nat Acad. Sci. USA 82:4360–4364 (1985). Thus, transient expression systems are particularly useful in the invention for expressing DNAs encoding amino acid sequence variants of AL-1, to identify those variants which are functionally active.

Since it is often difficult to predict in advance the characteristics of an amino acid sequence variant of AL-1, it will be appreciated that some screening of such variants will be needed to identify those that are functionally active. Such screening may be performed in vitro, using routine assays for receptor binding, or assays for axonal growth or development, or using immunoassays with monoclonal antibodies that selectively bind to AL-1 that is functionally active AL-1, such as a monoclonal antibody that selectively binds to the active site or receptor binding site of AL-1.

As used herein, the terms "transformation" and "transfection" refer to the process of introducing a desired nucleic acid, such a plasmid or an expression vector, into a host cell. Various methods of transformation and transfection are available, depending on the nature of the host cell. In the case of $E. coli$ cells, the most common methods involve treating the cells with aqueous solutions of calcium chloride and other salts. In the case of mammalian cells, the most common methods are transfection mediated by either calcium phosphate or DEAE-dextran, or electroporation. Sambrook, et al., eds., *Molecular Cloning*, pp. 1.74–1.84 and 16.30–16.55 (Cold Spring Harbor Laboratory Press, 1989). Following transformation or transfection, the desired nucleic acid may integrate into the host cell genome, or may exist as an extrachromosomal element.

Host cells that are transformed or transfected with the above-described plasmids and expression vectors are cultured in conventional nutrient media modified as is appropriate for inducing promoters or selecting for drug resistance or some other selectable marker or phenotype. The culture conditions, such as temperature, pH, and the like, suitably are those previously used for culturing the host cell used for cloning or expression, as the case may be, and will be apparent those skilled in the art.

Suitable host cells for cloning or expressing the vectors herein are prokaryotes, yeasts, and higher eukaryotes, including insect, vertebrate, and mammalian host cells. Suitable prokaryotes include eubacteria, such as Gram-negative or Gram-positive organisms, for example, *E. coli*, Bacillus species such as *B. subtilis*, Pseudomonas species such as *P. aeruginosa*, *Salmonella typhimurium*, or *Serratia marcescans*.

In addition to prokaryotes, eukaryotic microbes such as filamentous fungi or yeast are suitable hosts for AL-1-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*, Beach and Nurse, Nature 290:140–142 (1981), *Pichia pastoris*, Cregg, et al., Bio/Technology 5:479–485 (1987); Sreekrishna, et al., Biochemistry 28:4117–4125 (1989), Neurospora crassa, Case, et al., Proc. Natl. Acad. Sci. USA 76:5259–5263 (1979), and Aspergillus hosts such as *A. nidulans*, Ballance, et al., Biochem. Biophys. Res. Commun. 112:284–289 (1983); Tilburn, et al., Gene 26:205–221 (1983); Yelton, et al., Proc. Natl. Acad. Sci. USA 81:1470–1474 (1984), and *A. niger*, Kelly, et al., EMBO J. 4:475–479 (1985).

Suitable host cells for the expression of AL-1 also are derived from multicellular organisms. Such host cells are capable of complex processing and glycosylation activities. In principle, any higher eukaryotic cell culture is useable, whether from vertebrate or invertebrate culture. It will be appreciated, however, that because of the species-, tissue-, and cell-specificity of glycosylation, Rademacher, et al., Ann. Rev. Biochem. 57:785–838 (1988), the extent or pattern of glycosylation of AL-1 in a foreign host cell typically will differ from that of AL-1 obtained from a cell in which it is naturally expressed.

Examples of invertebrate cells include insect and plant cells. Numerous baculoviral strains and variants and corresponding permissive insect host cells from hosts such as *Spodoptera frugiperda* (caterpillar), *Aedes aegypti* (mosquito), *Aedes albopictus* (mosquito), Drosophila melanogaster (fruitfly), and *Bombyx mori* host cells have been identified. Luckow, et al., Bio/Technology 6:47–55 (1988); Miller, et al., in Genetic Engineering, vol. 8, pp.277–279 (Plenum Publishing, 1986); Maeda, et al., Nature 315:592–594 (1985).

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously altered to contain AL-1 DNA. During incubation of the plant cells with *A. tumefaciens*, the DNA encoding the AL-1 is transferred into cells, such that they become transfected, and will, under appropriate conditions, express the AL-1 DNA. In addition, regulatory and signal sequences compatible with plant cells are available, such as the nopaline synthase promoter and polyadenylation signal sequences, and the ribulose biphosphate carboxylase promoter, Depicker, et al., J. Mol. Appl. Gen. 1:561–573 (1982). Herrera-Estrella, et al., Nature 310:115–120 (1984). In addition, DNA segments isolated from the upstream region of the T-DNA 780 gene are capable of activating or increasing transcription levels of plant-expressible genes in recombinant DNA-containing plant tissue. European Pat. Pub. No. EP 321,196 (published Jun. 21, 1989).

However, interest has been greatest in vertebrate cells, and propagation of vertebrate cells in culture (tissue culture) has become a routine procedure in recent years. Kruse & Patterson, eds., *Tissue Culture* (Academic Press, 1973). Examples of useful mammalian host cells are the monkey kidney CV1 line transformed by SV40 (COS-7, ATCC CRL 1651); human embryonic kidney line 293 (or 293 cells subcloned for growth in suspension culture), Graham, et al., J. Gen Virol. 36:59–72 (1977); baby hamster kidney cells (BHK, ATCC CCL 10); Chinese hamster ovary cells (including DHFR-deficient CHO cells, Urlaub, et al., Proc. Natl. Acad. Sci. USA 77:4216–4220 (1980); mouse sertoli cells (TM4, Mather, Biol. Reprod. 23:243–251 (1980); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather, et al., Annals N. Y. Acad. Sci. 383:44–68 (1982)); MRC 5 cells; FS4 cells; and a human hepatoma line (Hep G2).

Construction of suitable vectors containing the nucleotide sequence encoding AL-1 and appropriate control sequences employs standard recombinant DNA methods. DNA is cleaved into fragments, tailored, and ligated together in the form desired to generate the vectors required.

For analysis to confirm correct sequences in the vectors constructed, the vectors are analyzed by restriction digestion (to confirm the presence in the vector of predicted restriction endonuclease) and/or by sequencing by the dideoxy chain termination method of Sanger, et al., Proc. Nat. Acad. Sci. USA 72:3918–3921 (1979).

The mammalian host cells used to produce the AL-1 of this invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham, et al., Meth. Enz. 58:44–93 (1979); Barnes, et al., Anal. Biochem. 102:255–270 (1980); Bottenstein, et al., Meth. Enz. 58:94–109 (1979); U.S. Pat. Nos. 4,560,655; 4,657,866; 4,767,704; or 4,927,762; or in PCT Pat. Pub. Nos. WO 90/03430 (published Apr. 5, 1990), may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in culture in vitro as well as cells that are within a host animal, for example, as a result of transplantation or implantation.

It is further contemplated that the AL-1 of this invention may be produced by homologous recombination, for example, as described in PCT Pat. Pub. No. WO 91/06667

(published May 16, 1991). Briefly, this method involves transforming cells containing an endogenous gene encoding AL-1 with a homologous DNA, which homologous DNA comprises (1) an amplifiable gene, such as DHFR, and (2) at least one flanking sequence, having a length of at least about 150 base pairs, which is homologous with a nucleotide sequence in the cell genome that is within or in proximity to the gene encoding AL-1. The transformation is carried out under conditions such that the homologous DNA integrates into the cell genome by recombination. Cells having integrated the homologous DNA then are subjected to conditions which select for amplification of the amplifiable gene, whereby the AL-1 gene amplified concomitantly. The resulting cells then are screened for production of desired amounts of AL-1. Flanking sequences that are in proximity to a gene encoding AL-1 are readily identified, for example, by the method of genomic walking, using as a starting point the AL-1 nucleotide sequence set forth in FIG. 2. Spoerel, et al., Meth. Enz. 152:598–603 (1987).

Gene amplification and/or gene expression may be measured in a sample directly, for example, by conventional Southern blotting to quantitate DNA, or Northern blotting to quantitate MRNA, using an appropriately labeled oligonucleotide hybridization probe, based on the sequences provided herein. Various labels may be employed, most commonly radioisotopes, particularly $^{32}$p. However, other techniques may also be employed, such as using biotin-modified nucleotides for introduction into a polynucleotide. The biotin then serves as the site for binding to avidin or antibodies, which may be labeled with a wide variety of labels, such as radioisotopes, fluorophores, chromophores, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of the gene product, AL-1. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu, et al., Am. J. Clin. Path., 75:734–738 (1980). Antibodies useful for immunohistochemical staining and/or assay of sample fluids may be either monoclonal or polyclonal. Conveniently, the antibodies may be prepared against a synthetic peptide based on the DNA sequences provided herein.

AL-1 preferably is recovered from the culture medium as a secreted polypeptide, although it also may be recovered from host cell lysates. To obtain AL-1 that is substantially free of contaminating proteins or polypeptides of the host cell in which it is produced it is necessary to purify the AL-1, based on the differential physical properties of AL-1 as compared to the contaminants with which it may be associated. For example, as a first step, the culture medium or lysate is centrifuged to remove particulate cell debris. AL-1 thereafter is purified from contaminant soluble proteins and polypeptides, for example, by ammonium sulfate or ethanol precipitation, gel filtration (molecular exclusion chromatography), ion-exchange chromatography, immunoaffinity chromatography, reverse phase HPLC, and/or gel electrophoresis. For example, AL-1 can be purified by immunoaffinity chromatography using a REK7-IgG resin (comprising REK7-IgG coupled to the resin material), as described in Example 5.

Amino acid sequence variants and derivatives of AL-1 are recovered in the same fashion, taking account of any distinguishing features or physical properties of the particular AL-1. For example, in the case of a fusion protein comprising AL-1 and another protein or polypeptide, such as a bacterial or viral antigen, a significant degree of purification may be obtained by using an immunoaffinity column containing antibody to the antigen. In any event, the ordinarily skilled artisan will appreciate that purification methods suitable for naturally occurring AL-1 may require modification to account for changes in the character of AL-1 or its variants or derivatives produced in recombinant host cells.

The purity of AL-1 produced according to the present invention is determined according to methods well known in the art, such as by analytical sodium dodecyl sulfate (SDS) gel electrophoresis, immunoassay, or amino acid composition or sequence analysis electrophoresis. Preferably, the AL-1 is purified to such an extent that it is substantially free of other proteins. For therapeutic uses, the purified AL-1 will be greater than 99% AL-1 and, accordingly, non-AL-1 proteins will comprise less than 1% of the total protein in the purified AL-1 composition.

AL-1 may be used as an immunogen to generate anti-AL-1 antibodies. Such antibodies, which specifically bind to AL-1, are useful as standards in assays for AL-1, such as by labeling purified AL-1 for use as a standard in a radioimmunoassay, enzyme-linked immunoassay, or competitive-type receptor binding assays radioreceptor assay, as well as in affinity purification techniques. Ordinarily, the anti-AL-1 antibody will bind AL-1 with an affinity of at least about $10^6$ L/mole, and preferably at least about $10^7$ L/mole.

Polyclonal antibodies directed toward AL-1 generally are raised in animals by multiple subcutaneous or intraperitoneal injections of AL-1 and an adjuvant. It may be useful to conjugate AL-1 or a peptide fragment thereof to a carrier protein that is immunogenic in the species to be immunized, such as keyhole limpet hemocyanin, serum albumin, bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (conjugation through lysine residues), glutaraldehyde, succinic anhydride, $SOCl_2$, or $R^1N=C=NR$, where R and $R^1$ are different alkyl groups.

Animals are immunized with such AL-1-carrier protein conjugates combining 1 mg or 1 µg of conjugate (for rabbits or mice, respectively) with 3 volumes of Freund's complete adjuvant and injecting the solution intradermally at multiple sites. One month later the animals are boosted with ⅕th to ¹⁄₁₀th the original amount of conjugate in Freund's complete adjuvant by subcutaneous injection at multiple sites. 7 to 14 days later animals are bled and the serum is assayed for anti-AL-1 antibody titer. Animals are boosted until the antibody titer plateaus. Preferably, the animal is boosted by injection with a conjugate of the same AL-1 with a different carrier protein and/or through a different cross-linking agent. Conjugates of AL-1 and a suitable carrier protein also can be made in recombinant cell culture as fusion proteins. Also, aggregating agents such as alum are used to enhance the immune response.

Monoclonal antibodies directed toward AL-1 are produced using any method which provides for the production of antibody molecules by continuous cell lines in culture. The modifier "monoclonal" indicates the character of the antibody as being obtained from a substantially homogeneous population of antibodies, and is not to be construed as requiring production of the antibody by any particular method. Examples of suitable methods for preparing monoclonal antibodies include the original hybridoma method of Kohler, et al., Nature 256:495–497 (1975), and the human B-cell hybridoma method, Kozbor, J. Immunol. 133:3001 (1984); Brodeur, et al., Monoclonal Antibody Production Techniques and Applications, pp.51–63 (Marcel Dekker, Inc., New York, 1987).

The monoclonal antibodies of the invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., U.S. Pat. No. 4,816,567; Morrison, et al., Proc. Natl. Acad. Sci. 81:6851–6855 (1984)).

In a preferred embodiment, the chimeric anti-AL-1 antibody is a "humanized" antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain.

Humanization can be performed following methods known in the art (Jones, et al., Nature 321:522–525 (1986); Riechmann, et al., Nature, 332:323–327 (1988); Verhoeyen, et al., Science 239:1534–1536 (1988)), by substituting rodent complementarity-determining regions (CDRs) for the corresponding regions of a human antibody. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, for example, Jakobovits, et al., Proc. Natl. Acad. Sci. 90: 2551–2555 (1993); Jakobovits, et al., Nature 362:255–258 (1993); Bruggermann, et al., Year in Immuno. 7:33 (1993). Human antibodies can also be produced in phage-display libraries (Hoogenboom, et al., J. Mol. Biol. 227:381 (1991); Marks, et al., J. Mol. Biol. 222:581 (1991).

For diagnostic applications, anti-AL-1 antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by David, et al., Biochemistry 13:1014–1021 (1974); Pain, et al., J. Immunol. Meth. 40:219–231 (1981); and Bayer, et al., Meth. Enz. 184:138–163 (1990).

The anti-AL-1 antibodies may be employed in any known assay method, such as competitive binding assays, direct and indirect sandwich assays, and immunoprecipitation assays. Zola, Monoclonal Antibodies: A Manual of Techniques, pp.147-158 (CRC Press, Inc., 1987).

Competitive binding assays rely on the ability of a labeled standard (e.g., AL-1 or an immunologically reactive portion thereof) to compete with the test sample analyte (AL-1) for binding with a limited amount of antibody. The amount of AL-1 in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David, et al., U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The anti-AL-1 antibodies of the invention also are useful for in vivo imaging, wherein an antibody labeled with a detectable moiety is administered to a host, preferably into the bloodstream, and the presence and location of the labeled antibody in the host is assayed. This imaging technique is useful in the staging and treatment of various neurological disorders. The antibody may be labeled with any moiety that is detectable in a host, whether by nuclear magnetic resonance, radiology, or other detection means known in the art.

Neutralizing anti-AL-1 antibodies are useful as antagonists of AL-1. The term "neutralizing anti-AL-1 antibody" as used herein refers to an antibody that is capable of specifically binding to AL-1, and which is capable of substantially inhibiting or eliminating the functional activity of AL-1 in vivo or in vitro. Typically a neutralizing antibody will inhibit the functional activity of AL-1 at least about 50%, and preferably greater than 80%, as determined, for example, by an in vitro receptor binding assay, or in vitro axon bundling assay, such as described in Example 8.

Other AL-1 antagonists are prepared using AL-1 receptor proteins, such as REK7. One example of an AL-1 antagonist is the REK7-IgG chimeric protein described herein. Another example of an AL-1 antagonist is a soluble form of an AL-1 receptor, which comprises the extracellular domain or the receptor substantially free of the transmembrane domain. The soluble form of the receptor can be used directly as an antagonist, or the receptor can be used to screen for small molecules that would antagonize AL-1 activity.

AL-1 is believed to be useful in promoting the development, maintenance, or regeneration of neurons in vivo, including central (brain and spinal chord), peripheral (sympathetic, prasympathetic, sensory, and enteric neurons), and motorneurons. Accordingly, AL-1 may be utilized in methods for the diagnosis and/or treatment of a variety of neurologic diseases and disorders.

In various embodiments of the invention, purified AL-1 can be administered to patients in whom the nervous system has been damaged by trauma, surgery, stroke, ischemia, infection, metabolic disease, nutritional deficiency, malignancy, or toxic agents, to promote the survival or growth of neurons. For example, AL-1 can be used to promote the survival or growth of motorneurons that are damaged by trauma or surgery. Also, AL-1 can be used to treat motorneuron disorders, such as amyotrophic lateral sclerosis (Lou Gehrig's disease), Bell's palsy, and various conditions involving spinal muscular atrophy, or paralysis. AL-1 can be used to treat human neurodegenerative disorders, such as Alzheimer's disease, Parkinson's disease, epilepsy, multiple sclerosis, Huntington's chorea, Down's Syndrome, nerve deafness, and Meniere's disease.

Further, AL-1 can be used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine.

In still further embodiments of the invention, AL-1 antagonists, and especially anti-AL-1 antibodies, can be administered to patients suffering from neurologic diseases and disorders characterized by excessive production of AL-1. AL-1 antagonists can be used in the prevention of aberrant regeneration of sensory neurons such as may occur post-operatively, or in the selective ablation of sensory neurons, for example, in the treatment of chronic pain syndromes.

Therapeutic formulations of AL-1 and AL-1 antagonists for treating neurologic diseases and disorders are prepared by mixing AL-1 or anti-AL-1 antibody, having the desired degree of purity, with optional physiologically acceptable carriers, excipients, or stabilizers which are well known. Acceptable carriers, excipients or stabilizers are nontoxic at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

It may be desirable to adsorb AL-1 onto a membrane, such as a silastic membrane, which can be implanted in proximity to damaged neural tissue, or to incorporate AL-1 into liposomes. PCT Pat. Pub. No. WO 91/04014 (published Apr. 4, 1991). In another embodiment, the AL-1 used for therapeutic effect is AL-1 covalently joined to another protein, such as an immunoglobulin domain (for example, to produce an AL1-IgG fusion protein).

AL-1 optionally is combined with or administered in concert with other neurotrophic factors to achieve a desired therapeutic effect. For example, AL-1 may be used together with NGF, NT-3, BDNF, NT-4/5, an insulin-like growth factor (e.g., IGF-1, IGF-2, or IGF-3) or another neurotrophic factor to achieve a synergistic stimulatory effect on the growth of sensory neurons, wherein the term "synergistic" means that the effect of the combination of AL-1 with a second substance is greater than that achieved with either substance used individually.

AL-1 and AL-1 antagonists to be used for in vivo administration must be sterile. This is readily accomplished by filtration of a solution of AL-1 or anti-AL-1 antibody through sterile filtration membranes. Thereafter, the filtered solution may be placed into a container having a sterile access port, for example, an intravenous solution bag or vial having a stopper pierceable by a hypodermic injection needle. The filtered solution also may be lyophilized to produce sterile AL-1 or anti-AL-1 antibody in a powder form.

Methods for administering AL-1 and AL-1 antagonists in viva include injection or infusion by intravenous, intraperitoneal, intracerebral, intrathecal, intramuscular, intraocular, intraarterial, or intralesional routes, and by means of sustained-release formulations.

Sustained-release formulations generally consist of AL-1 or AL-1 antagonists and a matrix from which the AL-1 or AL-1 antagonists are released over some period of time. Suitable matrices include semipermeable polymer matrices in the form of shaped articles, for example, membranes, fibers, or microcapsules. Sustained release matrices may comprise polyesters, hydrogels, polylactides, U.S. Pat. No. 3,773,919, copolymers of L-glutamic acid and gamma ethyl-L-glutamate, Sidman, et al., Biopolymers, 22: 547–556 (1983), poly (2-hydroxyethyl-methacrylate), or ethylene vinyl acetate, Langer, et al., J. Biomed. Mater. Res. 15: 167–277 (1981); Langer, Chem. Tech. 12:98–105 (1982).

In one embodiment of the invention, the therapeutic formulation comprises AL-1 or AL-1 antagonist entrapped within or complexed with liposomes. For example, AL-1 covalently joined to a glycophosphatidyl-inositol moiety may be used to form a liposome comprising AL-1. In a further embodiment, the therapeutic formulation comprises cells actively producing AL-1 or AL-1 antagonist. Such cells may be directly introduced into the tissue of a patient, or may be encapsulated within porous membranes which are then implanted in a patient, in either case providing for the delivery of AL-1 or anti-AL-1 antagonist into areas within the body of the patient in need of increased or decreased concentrations of AL-1. Alternatively, an expression vector comprising AL-1 DNA may be used for in vivo transformation of a patient's cells to accomplish the same result.

An effective amount of AL-1 or anti-AL-1 antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Where possible, it is desirable to determine appropriate dosage ranges first in vitro, for example, using assays for neuronal cell survival or growth which are known in the art, and then in suitable animal models, from which dosage ranges for human patients may be extrapolated. In a specific embodiment of the invention, a pharmaceutical composition effective in promoting the survival or growth of neurons will provide a local GPA concentration in vivo of between about 0.1 and 10 ng/ml.

In summary, by providing nucleic acid molecules encoding AL-1, the present invention enables for the first time the production of AL-1 by recombinant DNA methods, thus providing a reliable source of sufficient quantities of AL-1 for use in various diagnostic and therapeutic applications. In view of its distinct biological properties, purified recombinant AL-1 will be especially useful in a variety of circumstances where it is necessary or desirable to assure neuronal growth and survival, but where other neurotrophic factors either cannot be used or are ineffective.

The following examples are offered by way of illustration only and are not intended to limit the invention in any manner. All patent and literature references cited herein are expressly incorporated.

EXAMPLE 1

Identification and Isolation of REK7 CDNA

To isolate novel growth factors that might act on central nervous system neurons, a search for new tyrosine kinase receptors was made using a polymerase chain reaction (PCR). Degenerate sense and antisense primers were prepared that corresponded to conserved amino acid sequences within the kinase domain of many receptor tyrosine kinases. The nucleotide sequences of the primers were as follows:

5'-CCCTCGAGGTCGACCAYMGIGAYYTIGCIRCIMGIAA-3'

(SEQ. ID. 5)

5'-CCCTCGAGGTCGACCAYMGIGAYYTIGCITGYMGIAA-3'

(SEQ. ID. 6)

5'-CCGCGGTGCGGCCGCCRWAISHCCAIACRTC-3' (SEQ. ID. 7)

These degenerate primers were used to amplify the cDNAs of an adult mouse hippocampal cDNA library using standard PCR methods, and the resulting amplified cDNAs were subcloned and sequenced. One of these cDNAs, approximately 200 bp in size, encoded a deduced amino acid sequence that appeared to be related to an amino acid sequence within the kinase domains of the eph family of receptor tyrosine kinases. This 200 bp CDNA then was used as a probe to isolate a full-length CDNA from a rat hippocampal CDNA library. FIG. 1 shows the nucleotide sequence (SEQ. ID NO. 1) of the full-length CDNA, and the deduced amino acid sequence (SEQ. ID NO. 2) of the encoded protein, termed REK7.

REK7 appears to be the rat homologue of cek7, and is closely related to ehk-1 and bsk. (Maisonpierre, et al., Oncogene 8:3277–3288 (1993); Zhou, et al., J. Neurosci. Res. 37:129–143 (1994)). In particular, the REK7 cDNA corresponds to a splice variant of ehk-1 lacking the first of two tandem fibronectin type-III domains.

EXAMPLE 2

Construction of REK7 Expression Plasmid

A cDNA encoding REK7 was cloned into the mammalian expression vector pRK7 (PCT Publication No. WO 90/02798, published Sep. 22, 1990), between the XbaI and BamHI restriction endonuclease cleavage sites of pRK7, to produce the expression plasmid pRK-REK7.

EXAMPLE 3

Production of REK7-IgG Fusion Protein

DNA encoding a soluble REK7-IgG chimera was constructed by joining DNAs encoding the extracellular domain of REK7 and the $F_c$ domain of the $IgG_1$ heavy chain. The DNA sequence encoding the $IgG_1$ portion of the REK7-IgG chimera was obtained from the CD4-IgG expression plasmid pRKCD4$_2$F$_{c1}$ (Capon, et al., Nature 337:525 (1989); Byrn, et al., Nature 344:667 (1990)). That plasmid encodes a hybrid polypeptide consisting of residues 1–180 of the mature human CD4 protein (two N-terminal CD4 variable domains) fused to the portion of the human immunoglobulin $IgG_1$ protein extending from the aspartic acid residue at position 216 (which is the first residue of the $IgG_1$ hinge after the cysteine residue involved in heavy-light chain bonding) to amino acid residue 441 (the numbering of residues in $IgG_1$ is based on amino acid residue 114 being the first residue of the heavy chain constant region (Kabat, et al., Sequences of Proteins of Immunological Interest, 4th ed. (1987)).

PCR was used to generate a 600 bp fragment containing sequences encoding the 3'-end of the REK7 extracellular domain (terminating at $Gln_{462}$, the junction between the extracellular domain and the transmembrane domain), joined to sequences encoding the 5'-end of a human $IgG_1$ Fc domain. The 600 bp fragment was constructed in three steps. First, a DNA fragment containing the 3'-end of the REK7 extracellular domain was amplified using pRK/EK7 as template and 5'-TCTGTGACAGACGATCCTCCC (primer 1, SEQ. ID. NO. 8) and 5'-GCACGGTGGACATGTGTGA GTTTTGTCCTGGCTTTGATCATTAGATGCTGCAAC (SEQ. ID. NO. 9) as primers. Second, a DNA fragment containing the 5'-end of a human $IgG_1$ Fc domain was amplified using pRKCD4-IgG as template and 5'-GTTGCAGCATCTAATGATCAAAGCCAGGACAAA ACTCACACATGTCCACCGTGC (SEQ. ID. NO. 10) and 5'-GCACTTGTACTCCTTGCC (primer 2, SEQ. ID. NO. 11) as primers. Finally, the two resulting amplified DNA fragments were mixed together and covalently joined in a third PCR using primers 1 and 2, to produce a 600 bp DNA fragment encoding a REK7-IgG fusion protein.

Since the REK7 cDNA appears to contain sequences that promote rearrangements and deletions during DNA manipulation, assembly of an expression plasmid encoding the full-length REK7-IgG protein was carried out in three steps. First, the 600 bp PCR product (see above) was cut by digestion with KpnI and SacII restriction endonucleases and the resulting KPNI-SacII fragment was gel purified. pRKCD4-IgG$_1$ was cleaved with HindIII and SacII restriction endonucleases and a 502 bp fragment was isolated. These KpnI-SacII fragment and the 502 bp fragment were ligated into a Bluescript vector (Stratagene, La Jolla, Calif. USA) cleaved with KpnI and HindIII, to produce REK7-IgG Intermediate 1.

Second, REK-IgG Intermediate 1 was cut with KpnI and EcoRI restriction endonucleases and the resulting 1000 bp fragment was isolated. pRK-REK7 was cut with KpnI and ApaI restriction endonucleases and a 786 bp fragment was isolated. The 1000 bp fragment and the 786 bp fragment were ligated into a Bluescript vector cut with ApaI and EcoRI, to produce REK7-IgG Intermediate 2.

Finally, the complete pRKREK-IgG expression plasmid (7004 bp) was assembled by ligation of the three fragments as follows. REK7-IgG Intermediate 2 was cut with PflMI and EcoRI restriction endonucleases and a 1860 bp fragment was isolated. pRK-REK7 was cut with PflMI and PstI restriction endonucleases and a 512 bp fragment was isolated. These two fragments were ligated to the pRK7 vector cut with PstI and EcoRI, to produce pRKREK7-IgG.

REK7-IgG was expressed in human embryonic kidney 293 cells [Graham, et al., *J. Gen. Virol.* 36, 59 (1977) and Chinese hamster ovary (CHO) cells by transient transfection using the calcium phosphate precipitation method as described by Capon, et al., supra, and Byrn, et al., supra. The REK7-IgG chimera was purified to greater than 95% homogeneity from serum free cell culture supernatants by affinity chromatography on immobilized *Staphylococcus aureus* Protein A as described by Capon, et al., supra.]

EXAMPLE 4

Identification of a Source for REK7 Ligand

In an effort to identify the putative REK7 ligand, REK7-IgG was used to screen cultured cell lines for cell surface expression of REK7-binding activity. Cell lines were assayed by incubation with REK7-IgG and fluorescent anti-IgG antibody followed by fluorescence-activated cell sorting (FACS).

For example, human breast carcinoma cell line BT20 (American type Culture Collection, Rockville, Md., USA) was grown in 50/50 (v/v) F12/DMEM low glucose medium, with 10% fetal calf serum (FCS) and 1 mM glutamine (collectively, growth medium), in a 5% $CO_2$. Cells at 80–90% confluence were harvested with 5 mM EDTA in phosphate buffered saline (PBS), counted and resuspended in binding buffer (50/50 (v/v) F12/DMEM low glucose medium, 5% FCS, and 1 mg/ml bovine serum albumin (BSA)) at a cell density of $5 \times 10^6$ cells/ml. To 1 ml of cells, 1 µg of REK7-IgG was added and incubated for 2 hours at room temperature. The cells then were collected by centrifugation, incubated with a fluorescein-labelled anti-human IgG1-Fc for 1 hour at room temperature, then analyzed by FACS.

The BT20 cell line and the human cervical carcinoma cell line HeLa (American type Culture Collection, Rockville, Md., USA) were found to specifically bind the REK7-IgG. Furthermore, pretreatment of these cells with phosphatidylinositol-specific phospholipase C prior to incubation with REK7-IgG was found to decrease the binding of the REK7-IgG, suggesting the REK7 ligand is linked to the cell membrane by a glycophosphatidyl-inositol (GPI) anchor.

EXAMPLE 5

Purification of REK7 Ligand from BT20 Cells

BT20 cells were grown to 80% confluence in 150 mm plates, harvested by 5 mM EDTA in PBS, and seeded into 850 mm² roller bottles with growth medium. After 1 week of growth the cells were nearly confluent. The growth medium was removed, the cells washed with PBS, and serum-free growth medium was added. After 5 days, conditioned medium was harvested (12 liters from 72 roller bottles), centrifuged, sterile filtered, concentrated in a 12 kD molecular weight cutoff Amicon filter, and stored at −70° C.

200 ml of BT20 conditioned media, concentrated as described above from 12 liters and frozen, was thawed, centrifuged at 17,000 rpm in a Sorvall SS34 rotor, and filtered through a 0.45 µm filter to clarify the solution. The 200 ml was pumped through a 2.0 ml CD4-IgG—Protein A (CD4-IgG covalently linked to Protein A through IgG moiety) immunoaffinity precolumn and a 1.0 ml REK7-IgG—Protein A (REK7-IgG covalently linked to Protein A through IgG moiety) immunoaffinity column in tandem with a flow rate of 0.5 ml/min. All chromatography was carried out at 4° C. Following one complete passage of the media through both columns, the flow rate was reduced to 0.2 ml/min, and the media was recycled through both columns. Following the loading of the REK7-IgG column, the two column were separated from each other, washed with 10 column volumes of PBS, and then eluted with four separate washes of 100 mM sodium citrate, pH 3.0 (2 ml each for the CD4-IgG column and 1 ml each for the REK7-IgG column). The first two washes were allowed to immediately flow through the column whereas the last two were incubated for 15 minutes before collection. The eluates were brought to pH 7.4 by the addition of 50 mM potassium phosphate, and an aliquot of each was analyzed by sodium dodecycl sulfate (SDS)-polyacrylamide gel electrophoresis (PAGE). Following silver staining of the gel, stained band of approximately 28,000, 27,000, and 25,000 Daltons was seen from the eluate from the last two washes, that were not seen in eluate obtained by similar treatment of the CD4-IgG precolumn.

EXAMPLE 6

Protein Sequencing

The 28,000, 27,000, and 25,000 Dalton protein bands that were observed on SDS-PAGE were transferred to a PVDF membrane (Millipore Corporation) by electroblotting, and then subjected to amino acid sequencing using a Applied Biosystems 473A or 470A sequencer. The N-terminus of each of the 28,000 and 25,000 Dalton proteins was blocked, but the N-terminus of the 27,000 Dalton protein gave the following sequence: DRYAVYW(N)SSNPRFQRGDYHIDVXINDY (SEQ. ID NO. 12).

Separate sequence analysis of the three protein bands after cyanogen bromide cleavage or digestion with Lys-C endopeptidase indicated that the 28,000, 27,000, and 25,000 Dalton proteins were related. In particular, the 27,000 Dalton and 25,000 Dalton proteins appeared to be proteolytic processed forms of the 28,000 Dalton protein. Sequence analysis of the 28,000 Dalton band after digestion with Lys-C endopeptidase resulted in two sequences, one of which was nearly identical to the N-terminal sequence of the 27,000 Dalton protein and also had three additional N-terminal residues, AVA. The following internal amino acid sequences were determined for cyanogen bromide and Lys-C fragments of the proteins:

MKTIGVHDRVFDVNDKVENXLEPA (SEQ. ID. NO. 13)

VNFDGYSAXDHTSKGFKRXEXNR (SEQ. ID. NO. 14)

FQLFTPFSLGXEXRXGREXFYISXAIP (SEQ. ID. NO. 15)

KRWECNRP (SEQ. ID. NO. 16)

EXAMPLE 7

Isolation of REK7 Ligand cDNA

Based on the above protein sequences obtained for the REK7 ligand, two degenerate PCR primers were synthesized for use in isolating CDNA encoding the REK7 ligand:

5'-CCCTCGAGGTCGACGAYMGITAYGCIGTNTAYTGGAA (SEQ. ID. NO. 17)

5'-CCGCGGTGCGGCCGCTCTAGARTAICCRTCRAARTTNACCAT (SEQ. ID. NO. 18).

These degenerate primers were used to amplify the cDNAs of a BT20 cell CDNA library using standard PCR methods, and two resulting amplified cDNAs were subcloned and sequenced. These cDNAs, approximately 180 bp and 135 bp in size, encoded deduced amino acid sequences matching the above amino acid sequences determined for the REK7 ligand. The 180 bp fragment was used to screen a human fetal brain cDNA library (containing approximately $2 \times 10^6$ clones) by hybridization under high stringency conditions. The nucleotide sequence determined from two independent positive CDNA clones is shown in FIG. 2, along with the deduced amino acid sequence of the REK7 ligand, termed AL-1.

EXAMPLE 8

Biological Activity

Cerebral cortex from postnatal day 2 (P2) Wistar rat pups was dissected in 4° C. Hanks balanced salt solution (HBSS, calcium and magnesium free) under sterile conditions. After initial trituration with a 10 ml pipette, cells were dissociated by two passages through an 18 gauge injection cannula attached to a 10 ml syringe. The cell suspension was strained through a 70 μm cell strainer (Falcon) and centrifuged at 800 g for 5 minutes. Pelleted cells were resuspended in 50/50 (v/v) DMEM/F12 with 10% fetal bovine serum, 15 mM HEPES pH7.4. The cell suspension was plated into 75 cm² tissue culture flasks, and placed into a 37° C., 5% $CO_2$ incubator. Cultures were grown to confluence (10–15 days) and the medium was changed every 3 days. Once cultures were confluent the flasks were shaken in a rotary shaker at 300 rpm at 37° C. for 24 hrs to obtain purified astrocytes. Media with the suspended cells and debris was replaced and cultures were incubated for another 24 hours. Purified astrocyte cultures were trypsinized (0.05% trypsin, 0.025 mM EDTA in Hanks) from the flasks and then replated into 60 mm tissue culture treated dishes (2 dishes per 75 cm² flask).

Cerebral cortex of embryonic day 16 (E16) rats was dissected in 4° C. HBSS under sterile conditions. Media was changed to 1 ml of Defined Neuronal Medium (DNM. Peterson et al., Dev. Brain Res. 48:187–195 (1989) and cortices were triturated by pipeting 15 times through a plastic disposable pipet blue. 9 ml of DNM then was added and the cell suspension was strained through a 45 μm cell strainer and centrifuged at 800 g for 5 minutes. Pelleted cells were resuspended in 5 ml of DNM and $4 \times 10^5$ cells were plated onto 60 mm dishes containing astrocytes which had been pretreated for 6 hours with either REK7-IgG (30 μg/ml), CD4-IgG (30 μg/ml), or no added IgG (control). Cultures were grown for 4 days and then fixed for 15 minutes with 4% paraformaldehyde in 100 mM Sodium Phosphate buffer, pH 7.4, followed by 3 washes with PBS.

The addition of REK7-IgG to the co-cultures completely prevented the formation of axon bundles. In contrast, the addition of CD4-IgG, and other IgGs had no effect on axon bundling. These results indicate a role for REK7 and its ligand, AL-1, in axon fasciculation, which is a crucial step in the development of the nervous system during regeneration following injury.

Consistent with that role, we also found that upon incubation of the cultured neuronal cells with labelled anti-REK7 antibodies, there was specific binding of the antibodies to the surface of axonal fibers within axon bundles. Furthermore, when cells expressing REK7 were incubated with AL-1, specific phosphorylation of REK7 was observed, indicating that AL-1 not only binds to REK7 but also activates REK7.

---

What is claimed is:

1. A method of determining the presence of an AL-1 nucleic acid sequence in a sample, comprising:
   (a) contacting a sample nucleic acid with a nucleic acid molecule which has at least 10 contiguous nucleotides selected from (i) nucleotides 323 to 1006 of SEQ ID NO: 3, (ii) the codons of a nucleic acid sequence encoding the amino acid sequence SEQ ID NO: 4, or (iii) an exact complementary nucleic acid sequence of (i) or (ii), and which hybridizes to the nucleic acid sequence of (i), (ii) or (iii);
   (b) hybridizing the nucleic acid molecule to the sample nucleic acid to create a hybrid molecule; and
   (c) determining the presence of AL-1 nucleic acid in the sample by means of the hybrid molecule.

2. The method of claim 1, wherein the nucleic acid molecule consists of at least 10 contiguous nucleotides selected from (i) nucleotides 323 to 1006, inclusive, of SEQ ID NO: 3, (ii) the codons of a nucleic acid sequence encoding the amino acid sequence SEQ ID NO: 4, or (iii) an exact complementary nucleic acid sequence of (i) or (ii), and which hybridizes to the nucleic acid sequence of (i), (ii) or (iii).

3. The method of claim 1, wherein the nucleic acid molecule has at least 10 contiguous nucleotides selected from nucleotides 323 to 1006 inclusive, of SEQ ID NO: 3 or an exact complementary sequence thereof.

4. The method of claim 1, wherein the nucleic acid molecule consists essentially of at least 10 contiguous nucleotides selected from (i) nucleotides 323 to 1006, inclusive, of SEQ ID NO: 3, (ii) the codons of a nucleic acid sequence encoding the amino acid sequence SEO ID NO: 4, or (iii) an exact complementary nucleic acid sequence of (i) or (ii), and which hybridizes to the nucleic acid sequence of (i), (ii) or (iii).

5. The method of claim 1, wherein the nucleic acid molecule has at least 15 nucleotides selected from (i), (ii) or (iii).

6. The method of claim 5, wherein the nucleic acid molecule has more than 25 nucleotides selected from (i), (ii) or (iii).

7. A method of amplifying a target AL-1 nucleic acid in a sample, comprising:
   (a) contacting the sample nucleic acid with a primer having at least 10 contiguous nucleotides selected from (i) nucleotides 323 to 1006 of SEQ ID NO: 3, (ii) the codons of a nucleic acid sequence encoding the amino acid sequence SEQ ID NO: 4, or (iii) an exact complementary nucleic acid sequence of (i) or (ii);

(b) hybridizing the primer to the nucleic acid sample; and, (c) performing an amplification reaction to amplify preferentially target AL-1 nucleic acid sequence within the sample.

8. The method of claim 7, wherein the primer hybridizes to (i), (ii), or (iii).

9. The method of claim 7, wherein the primer has at least 10 contiguous nucleotides selected from nucleotides 323 to 1006, inclusive of SEQ ID NO: 3 or an exact complementary sequence thereof.

10. The method of claim 9, wherein the primer consists essentially of at least 10 contiguous nucleotides selected from (i) nucleotides 323 to 1006, inclusive, of SEQ ID NO: 3, (ii) the codons of a nucleic acid sequence encoding the amino acid sequence SEQ ID NO: 4, or (iii) an exact complementary nucleic acid sequence of (i) or (ii), and which hybridizes to the nucleic acid sequence of (i), (ii) or (iii).

11. The method of claim 7, wherein the primer has at least 15 nucleotides selected from (i), (ii) or (iii).

12. The method of claim 11, wherein the primer has more than 25 nucleotides selected from (i), (ii) or (iii).

13. The method of claim 7, which further comprises the steps of:

(a) contacting the sample nucleic acid with a second primer having at least 10 contiguous nucleotides selected from (i) nucleotides 323 to 1006 of SEQ ID NO: 3, (ii) the codons of a nucleic acid sequence encoding the amino acid sequence SEQ ID NO: 4, or (iii) an exact complementary nucleic acid sequence of (i) or (ii); and (b) hybridizing the second primer to the sample nucleic acid.

14. The method of claim 13, wherein the second primer hybridizes to (i), (ii), or (iii).

15. The method of claim 13, wherein the second primer has at least 10 contiguous nucleotides selected from nucleotides 323 to 1006 of SEQ ID NO: 3 or an exact complementary sequence thereof.

16. The method of claim 15, wherein the second primer consists essentially of at least 10 contiguous nucleotides selected from (i) nucleotides 323 to 1006, inclusive, of SEQ ID NO: 3, (ii) the codons of a nucleic acid sequence encoding the amino acid sequence SEQ ID NO: 4, or (iii) an exact complementary nucleic acid sequence of (i) or (ii), and which hybridizes to the nucleic acid sequence of (i), (ii) or (iii).

17. The method of claim 13, wherein the second primer has at least 15 nucleotides selected from (i), (ii) or (iii).

18. The method of claim 17, wherein the second primer has more than 25 nucleotides selected from (i), (ii) or (iii).

* * * * *